US005705660A

United States Patent [19]
Berkowitz et al.

[11] Patent Number: 5,705,660
[45] Date of Patent: Jan. 6, 1998

[54] METHOD FOR THE SYNTHESIS OF α-OXIRANYL AMINO ACIDS

[75] Inventors: David B. Berkowitz; Michelle L. Pedersen, both of Lincoln, Nebr.

[73] Assignee: Board of Regents, University of Nebraska-Lincoln

[21] Appl. No.: 295,350

[22] Filed: Aug. 22, 1994

[51] Int. Cl.$^6$ .................................................. C07D 301/02
[52] U.S. Cl. .......................... 549/518; 549/524; 549/525; 562/553; 562/564
[58] Field of Search ................... 549/512, 518, 549/524, 525; 536/27.31; 562/553, 564

[56] References Cited

U.S. PATENT DOCUMENTS

| | | | |
|---|---|---|---|
| 3,960,927 | 6/1976 | Metcalf et al. | 560/38 |
| 4,147,873 | 4/1979 | Metcalf et al. | 546/221 |
| 4,183,858 | 1/1980 | Metcalf et al. | 548/495 |
| 4,418,075 | 11/1983 | Tamai et al. | 514/475 |
| 5,190,969 | 3/1993 | Blumenstein et al. | 514/422 |

OTHER PUBLICATIONS

Marks et al., *Basic Medical Biochemistry*, Williams & Wilkins, Baltimore, MD, 1996, only pp. 62–63 supplied. Month of publication data is unavailable. Issue No. has been included whenever possible.
Schultz et al., "Proteins I: Composition and Structure" in *Textbook of Biochemistry*, 3rd Ed., Devlin (ed.), Wiley-Liss, New York, NY, 1992, only pp. 25–33 supplied. Month of publication data is unavailable. Issue No. has been included whenever possible.
Kochetkov et al., *Organic Chemistry of Nucleic Acids, Part A*, Plenum Press, New York, 1971, pp. 334–338 & 347–348.
Kochetkov et al., *Organic Chemistry of Nucleic Acids, Part B*, Plenum Press, New York, 1972, pp. 412–419 & 423.
Kochetkov et al., *Organic Chemistry of Nucleic Acids, Part B*, Plenum Press, New York, 1972, pp. 466–470 & 475–476.
Pedersen et al., "Formal α-Vinylation of Amino Acids. Use of a New Benzeneselenolate Equivalent," *J. Organic Chem.*, 58(25), 6966–6975 (1993).
Berkowitz et al., "Simultaneous Amino and Carboxyl Group Protection by a-Branched Amino Acids," *J. Organic Chem.*, 59(18), 5476–5478 (1994).
Neubauer et al., "Asymmetric Synthesis via Heterocyclic Intermediates, XXVI. Asymmetric Synthesis of an Amino Acid Ester with a 3,4-Epoxy Function (β,γ-Epoxy Function) by the Bislactim Ether Method," *Liebigs Ann. Chem.*, 1985, 1508–1511.
Sailer et al., "Flavovirin—A New Antifungal Antibiotic Produced by the Pyrenomycete *Melanoconis flavirens*," *J. Basic Microbiol.*, 29(6), 375–381 (1989).
Sawada et al., "Synthesis of Labeled (±)-2-Amino-3-butenoic Acids," *J. Organic Chem.*, 51(17), 3384–3386 (1986).

Chenault et al., "Kinetic Resolution of Unnatural and Rarely Occurring Amino Acids: Enantioselective Hydrolysis of N-Acyl Amino Acids Catalyzed by Acylase I," *J. Am. Chem. Soc.*, 111(16), 6345–6374 (1989).
Kim et al., "A Simple and Mild Esterification Method for Carboxylic Acids Using Mixed Carboxylic–Carbonic Anhydrides," *J. Organic Chem.*, 50(5), 560–565 (1985).
Cook et al., "Steroids. LXXIX. Synthesis and Reactions of Oxiranes Obtained from 3– and 17–Keto Steroids," *J. Organic Chem.*, 33(7), 2789–2793 (1968).
Kashino et al., "Structures of 3β– and 17β–Oxirane Inhibitors of 3–Oxo–$\Delta^5$–steroid Isomerase," *J. Am. Chem. Soc.*, 109(22), 6765–6771 (1987).
Yarlett et al., "Inhibition of *Trichomonas vaginalis* Ornithine Decarboxylase by Amino Acid Analogs," *Biochem. Pharmacology*, 44(2), 243–250 (1992).
Danzin et al., "α–Ethynyl and α–Vinyl Analogues of Ornithine and Enzyme–Activated Inhibitors of Mammalian Ornithine Decarboxylase," *J. Medicinal Chem.*, 24(1), 16–20 (1981).
Murray-Rust et al., "Directional Hydrogen Bonding to $sp^2$ and $sp^3$–Hybridized Oxygen Atoms and Its Relevance to Ligand–Macromolecule Interactions," *J. Am. Chem. Soc.*, 106(4), 1018–1025 (1984).
Metcalf et al. (IV), "Synthesis of βγ–Unsaturated Amino Acids as Potential Catalytic Irreversible Enzyme Inhibitors," *Tetrahedron. Letters*, 1977(41), 3689–3692.
Castelhano et al., "Synthesis of a–Amino Acids with βγ–Unsaturated Side Chains," *Tetrahedron*, 44(17), 5451–5466 (1988).
Fitzner et al., "Synthesis of Protected Racemic βγ–Unsaturated–α–Amino Acids via γ–Phenylseleno–α, β–Unsaturated Esters," *Tetrahedron. Letters*, 26(16), 1959–1962 (1985).
Taub et al., "Synthesis of α–Ethynyl–3,4–Dihydroxyphenylalanine and α–Vinyl–3,4–Dihydroxyphenylalanine," *Tetrahedron. Letters*, 1977(32), 2745–2748.
Huldrik et al., "α–Silyl Aldehydes: Preparation and Use as Stereoselective Vinyl Cation Equivalents," *J. Am. Chem. Soc.*, 103(20), 6251–6253 (1981).
Steglich et al., "Überführung von α–Aminosäuren in α–Vinylaminosäuren," *Synthesis*, 1980, 481–483.
Metcalf et al. (V), "Phenyl trans–2–Chlorovinyl Sulphone, a Vinyl Cation Equivalent," *J. Chem. Soc., Chem. Comm.*, 1978, 914–915.
Turk et al., "Studies with a α–Methyl Amino Acids. Resolution and Amino Protection," *J. Organic Chem.*, 40(7), 953–955 (1975).

*Primary Examiner*—John Kight
*Assistant Examiner*—L. Eric Crane
*Attorney, Agent, or Firm*—Suiter & Associates PC

[57] ABSTRACT

The present invention is related to a novel class of decarboxylase enzyme inhibitors consisting of α-oxiranyl amino acids and derivatives thereof and a method of synthesizing such compounds.

8 Claims, No Drawings

METHOD FOR THE SYNTHESIS OF α-OXIRANYL AMINO ACIDS

GOVERNMENT RIGHTS

The chemistry described in this application was not carried out under any grant or contract. However, it is the subject of pending grant applications at the NIH (No. 1R29CA62034-01A1) and at the American Cancer Society (No. JFRA C-75777).

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

CROSS REFERENCES

1. Related Applications

The present application is an original patent application and is currently not known to be related to any co-owned and co-pending application.

TECHNICAL FIELD

The invention describes (1) α-amino acids bearing an oxirane ring on the alpha carbon in place of the α-proton and (2) a method for synthesizing such amino acid derivatives. The object of this invention is to provide new mechanism-based inhibitors for enzymes of the amino acid decarboxylase class which cause inactivation via an enzyme catalyzed decarboxylation/ring opening sequence. The crucial ring opening step is to be greatly facilitated by (1) hydrogen bonding between the epoxide oxygen and the catalytically essential enzymatic general acid; and (2) relief of ring strain. Neither of these features have been incorporated into previously described amino acid decarboxylase inhibitors. Both are expected to lead to potent, specific and stringently mechanism-based inhibition.

BACKGROUND OF THE INVENTION a. Mechanism of Inhibition

The class of enzymes known as amine acid decarboxylases (DC's) is of great interest from both a mechanistic and a therapeutic point of view. Mechanistically, this enzymatic family presents a curious dichotomy. Nature has chosen two very different co-factors to facilitate cleavage of the $C_\alpha\text{-}CO_2$ bond. Pyridoxal phosphate is used by the vast majority of amino acid decarboxylases studied to date. However, some enzymes, such as S-adenosylmethionine decarboxylase (SAM DC), use pyruvamide to achieve the same task. It is generally accepted that both cofactors form Schiff bases with the α-amino group of substrate and act as electron sinks, providing for delocalization of the negative charge in the nascent α-carbanion formed upon enzymatic decarboxylation. Overall, each catalyzes the net loss of $CO_2$ from, and addition of a proton to, the α-carbon. With the exception of meso-diaminopimelate decarboxylase, all amino acid decarboxylases studied perform this sequence with retention of configuration. It is also noteworthy that while a few irreversible inhibitors have been developed for pyruvamide dependent decarboxylases (e.g. SAM DC), these inhibitors lack carboxyl groups. Decarboxylation-dependent irreversible inhibitors for pyruvamide-dependent decarboxylases have not yet been developed.

In seeking to develop irreversible, enzyme-activated inhibitors, the general strategy has been to divert the nascent α-carbanion from α-protonation (i.e. turnover) in one of two ways: (1) by placing a leaving group (typically fluoride or chloride) at the β-carbon (α-halogenmethyl amino acids); or (2) by placing a π-system adjacent to the carbanion (α-vinyl, α-ethynyl and α-allenyl amino acids), The most important members of these inhibitor classes are collected in Table 1 (below).

TABLE 1

Known Mechanism-Based Inhibitors of Amino Acid Decarboxylases

| Enzyme | Enzyme Comm. No. | Inhibitor(s) | Potential Application |
|---|---|---|---|
| L-DOPA Decarboxylase | E.C. 4.1.1.28 | 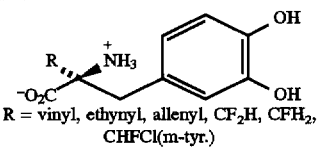<br>R = vinyl, ethynyl, allenyl, $CF_2H$, $CFH_2$, CHFCl(m-tyr.) | antihypertensive, Parkinson's disease (DOPA comb. therapy) |
| L-Ornithine Decarboxylase | E.C. 4.1.1.17 | 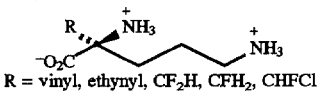<br>R = vinyl, ethynyl, $CF_2H$, $CFH_2$, CHFCl | antineoplastic, treatment of trypanosomiasis and pneumonia |
| S-Adenosyl-Methionine Decarboxylase (Pyruvamide) | E.C. 4.1.1.50 | 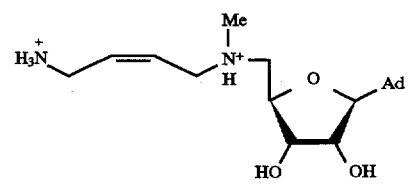 | antineoplastic, treatment of trypanosomiasis |
| L-Lysine Decarboxylase | E.C. 4.1.1.18 | 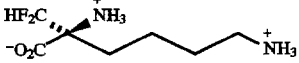 | antimycoplasmic |

TABLE 1-continued

Known Mechanism-Based Inhibitors of Amino Acid Decarboxylases

| Enzyme | Enzyme Comm. No. | Inhibitor(s) | Potential Application |
|---|---|---|---|
| L-Histidine Decarboxylase (PLP, pyruvamide) | E.C. 4.1.1.22 | | antihistamine, antineoplastic |
| L-Arginine Decarboxylase | E.C. 4.1.1.19 | R = $CFH_2$, $CF_2H$ | antibiotic, antiproliferative |
| L-Glutamate Decarboxylase | E.C. 4.1.1.15 | R = vinyl, CHFCl | investigative tool; reduction of brain GABA levels |

α-Allenic-DOPA is a more effective inhibitor (shorter t-½, more complete inactivation) than either α-vinyl- or α-ethylyl-DOPA, although all three inactivate DOPA DC. This result shows that substitution of a three-carbon unit in place of the α-proton is quite tolerable, at least for DOPA DC.

The stereospecificity of inhibition has been studied for several of the α-halogenmethyl amino acids and is highly variable. For αfluoromethyl DOPA, only the expected (S)-antipode inhibits DOPA DC. But for α-fluoromethylhistamine the unexpected (S)-antipode is the more potent inhibitor of histidine DC. For α-chlorofluoromethylornithine, all four possible stereoisomers irreversibly inhibit ornithine DC, all with t-½'s between 2 and 4 minutes. The enantiospecificity of inhibition of the α-vinyl amino acids has yet to be determined.

The prior art discloses only three labeling studies involving irreversible inhibitors for amino acid decarboxylases in which the chemical nature of the covalent enzyme-inhibitor or cofactor-inhibitor adduct has been investigated. Glutamate decarboxylase inactivation by L-serine O-sulfate represents the original case in which Metzler put forth his enamine mechanism.(Likos, J. J.; Ueno, H.; Feldhaus, R. W.; Metzler, D. E. "A Novel Reaction of the Coenzyme of Glutamate Decarboxylase with L-Serine O-Sulfate," Biochemstry 1984, 23:5188–5194). However, this inhibitor is not stringently mechanism-based as it functions via enzyme-catalyzed β-elimination rather than decarboxylation. On the other hand, β-fluoromethylhistidine is a good example of a mechanism-based decarboxylase inhibitor that also apparently follows a Metzler enamine mechanism (See Scheme 1 shown below).(Hayashi, H.; Tanase, S.; Snell, E. E. "Pyridoxal 5'-Phosphate -dependent Histidine Decarboxylase; Inactivation by α-Fluoromethylhistidine," J. Biol. Chem. 1986, 261, 11003–11009).

Scheme 1

Metzler Enamine Mechansim

Proposed Mechanism of Histidine Decarboxylase Inactivation by α-Fluoromethylhistidine

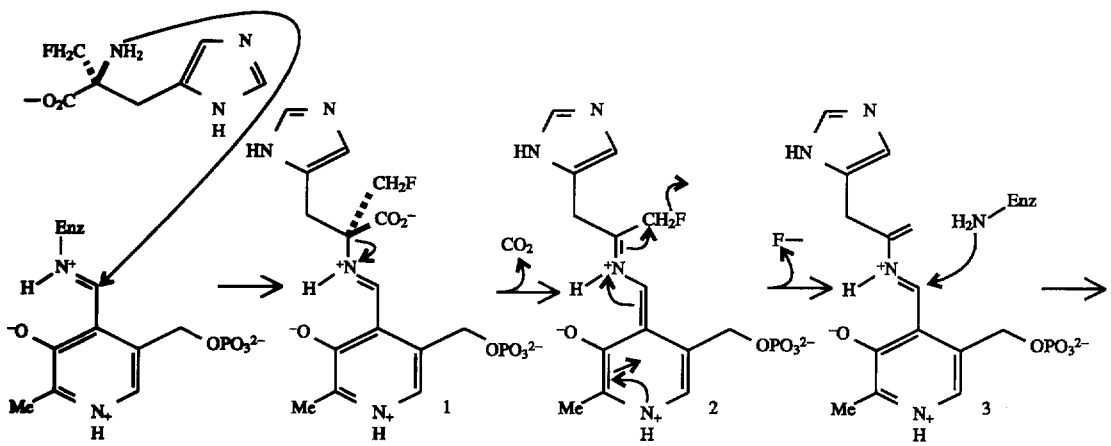

-continued
Scheme 1
Metzler Enamine Mechansim
Proposed Mechanism of Histidine Decarboxylase Inactivation by α-Fluoromethylhistidine

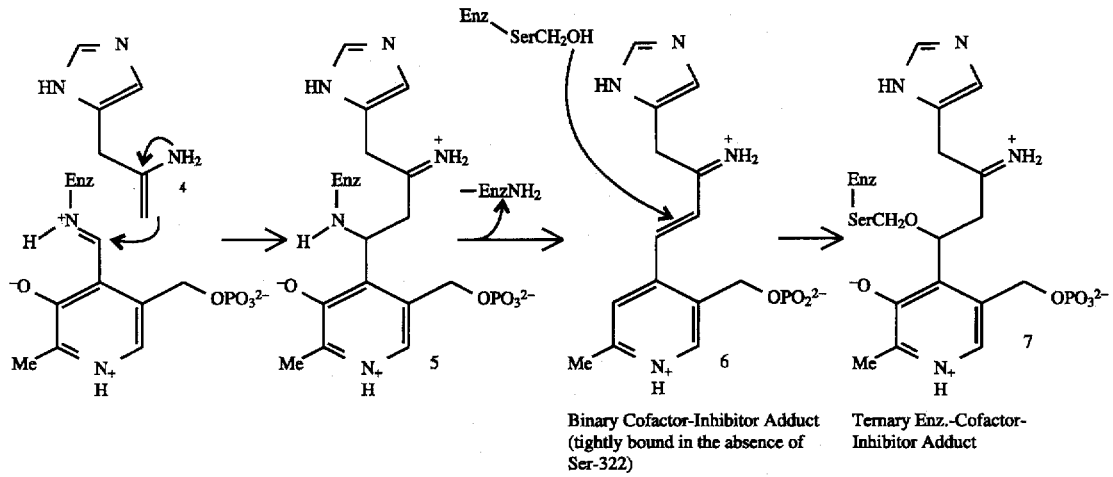

Binary Cofactor-Inhibitor Adduct (tightly bound in the absence of Ser-322)

Ternary Enz.-Cofactor-Inhibitor Adduct

The postulated mechanism of action of α-fluoromethylhistidine involves enzyme-catalyzed decarboxylation followed by β-fluoride-elimination. Transaldimination with an enzymatic lysine residue apparently ensues, leading to release of enamine 4. Nucleophilic attack of this enamine upon C-4 of the lysylpyridoximine results in the formation of a ternary enzyme-cofactor-inhibitor adduct 5. However, 5 can break down via a retro-Michael addition to release the enzymatic lysine residue and give a binary cofactor-inhibitor adduct 6. In certain cases binary adducts of this type (or the corresponding ketones) are released from the enzyme. In this case, the binary adduct is apparently intercepted via Michael addition of serine-322 in the wild-type enzyme. However, Snell's group has shown that the corresponding Ser→Ala322 mutant is also essentially irreversibly inactivated by α-fluoromethylhistidine. They propose avid noncovalent binding of the pyridoxylidene imine 6 (or the corresponding ketone) to the enzyme to account for this result. Other (non-decarboxylating) PLP-linked enzymes, for which evidence in support of a Metzler enamine mechanism has been obtained, include aspartate aminotransferase (serine O-sulfate), ornithine aminotransferase (4-aminohex-5-ynoate), γ-aminobutyrate transaminase (4-amino-5-fluoropentanoate and 4-aminohex-5-enoate), and alanine racemase (β-fluoroalanine, β-chloroalanine and O-acetylserine).

In the case of ornithine decarboxylase inhibition by difluoromethylornithine (DFMO), labeling studies support a Michael addition-elimination pathway (See Scheme 2 shown below) (Poulin, R.; Lu, L.; Ackermann, B.; Bey, P.; Pegg, A. E., "Mechanism of the Irreversible Inactivation of Mouse Ornithine Decarboxylase by α-Difluoromethylornithine." J. Biol Chem. 1992, 265, 150–158). The trapped enzyme nucleophile in this case is a cysteine residue. A related Michael addition-elimination, in which lysine-38 is the enzyme nucleophile, appears to be operative in the inhibition of alanine racemase by β-trifluoroalanine (Faraci, W. S.; Walsh, C. T., "Mechanism of Inactivation of Alanine Racemase by β,β,β-Trifluoroalanine." Biochemistry 1989, 28:431–437).

Scheme 2
Michael Addition-Elimination Mechanism
Proposed Mechanism of Ornithine Decarboxylase Inactivation by α-difluoromethylornithine

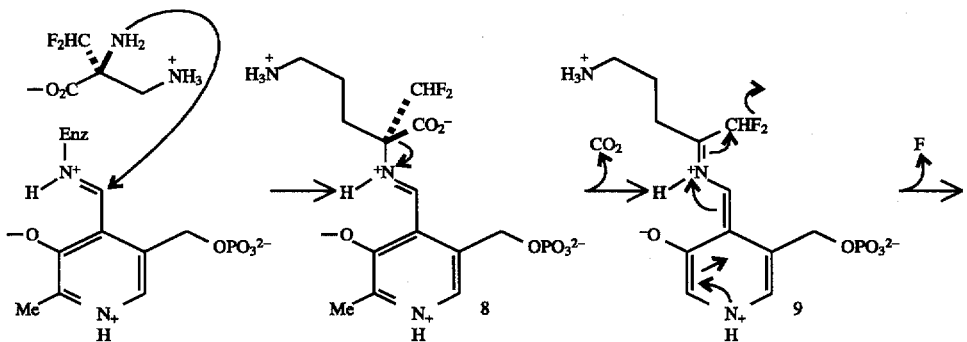

-continued
Scheme 2
Michael Addition-Elimination Mechanism
Proposed Mechanism of Ornithine Decarboxylase Inactivation by α-difluoromethylornithine

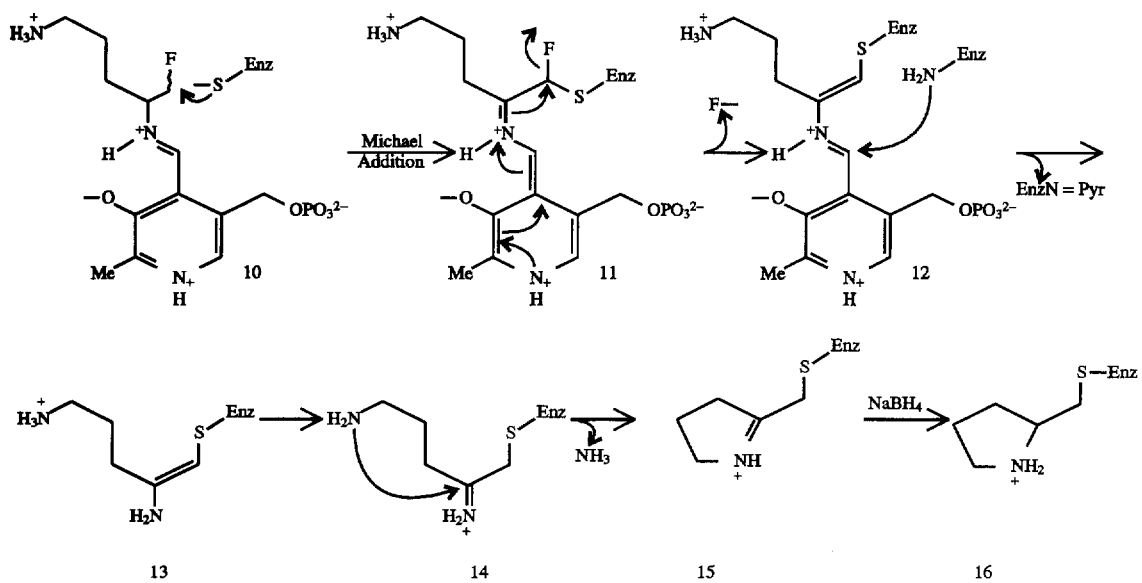

b. Therapeutic Potential.

From a medicinal point of view, several enzymes in this class are very important targets for the development of specific inhibitors. DOPA decarboxylase is the target of the important commercial drug α-methyl-DOPA used to treat hypertension. Peripheral DOPA DC inhibitors are used in combination therapy with L-DOPA for the treatment of Parkinsonism. Inhibitors of lysine DC are potential antimycoplasmic agents. As arginine DC is found in bacterial, but not in mammalian systems, arginine DC inhibitors are potential antibiotics. Inhibitors of histidine DC, ornithine DC and SAM DC all have potential as antitumor agents. In particular, the latter two enzymes control flux through the polyamine pathway. They are induced in response to various trophic influences and are essential for rapid cell proliferation. Indeed, inhibitors of these enzymes have proven to be potent antiproliferative agents in tissue culture. A SAM DC inhibitor cures African sleeping sickness in mice and α-difluoromethylornithine is effective against the microorganism that produces pneumonia in AIDS patients. However, the effectiveness of these compounds as drugs is often compromised by compensatory mechanisms triggered by tumor cells [i.e.ornithine DC gene amplification or replacement of putrescine (ornithine DC product) with cadaverine (lysine DC product)]. This has stimulated the development of SAM DC inhibitors as potential antineoplastics, to be used in combination with ornithine DC inactivators. But most importantly, the reality of such tumor cell compensatory mechanisms underlines the need to develop DC inhibitors of fundamentally new structural classes.

BRIEF SUMMARY OF THE INVENTION

The present invention provides a new class of irreversible inhibitors for amino acid decarboxylases in which the α-proton is formally replaced with an oxirane ring. This design introduces a new stereocenter and so both erythro and threo diastereomers, as defined below are possible.

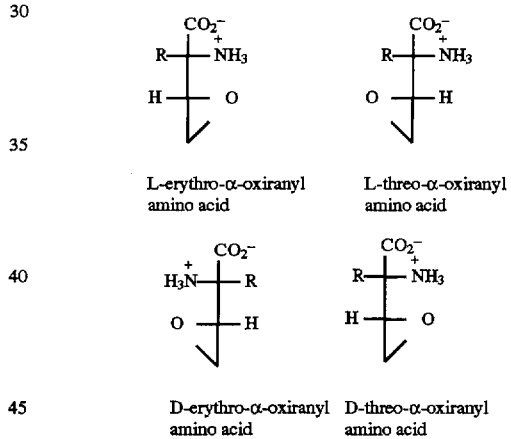

Synthesis involves the formal epoxidation of α-vinyl amino acids to yield α-oxiranyl amino acids via a three to five step process wherein α-vinyl amino acids are synthetic precursors. Several of these precursors have been shown to be irreversible inhibitors of the corresponding decarboxylases. Racemic α-vinyl amino acids are available from the corresponding amino acids. See Berkowitz and Pedersen, "Formal α-Vinylation of Amino Acids. Use of a New Benzeneselenolate Equivalent," Journal of Organic Chemistry 58:6966–6975 (1993) and references cited therein.

The conversion of these α-vinyl amino acids to α-oxiranyl amino acids involves a new single step synthetic procedure wherein hydrogenolytically cleavable protecting groups are simultaneously installed on the amino, carboxyl and side chain (hydroxyl or amino) functional groups of the free vinyl amino acids. Using these fully protected vinyl amino acids, free α-oxiranyl amino acids have been synthesized. Due to diastereomer separation problems, two different synthetic paths have been developed: (1) direct alkene epoxidation and (2) dihydroxylation, mesylation and displacement. In this way, the diastereomerically homogeneous, threo and erythro, α-oxiranyl amino acids derived from valine, phenylalanine and alanine have been obtained. Other members of the α-oxiranyl class may be produced under a similar procedure.

The process disclosed herein describes the first successful method of synthesizing fully deprotected α-oxiranyl amino acids. While U. Schöllkopf reported in 1985 the synthesis of an α-amino acid ester, in which a phenyl-substituted oxirane ring replaced the alpha proton, Schökopf was unable to deprotect the carboxyl group without affecting the oxirane ring.(Neubauer, H. J.; Baeze, J.; Freer, J. and Schöllkopf, "Asymmetric Synthesis of an Amino Acid Ester with a 3,4-Epoxy Function (β, γ-Epoxy Function) by the Bislactim Ether Method," *Liebigs Ann. Chem.* 1508–1511 (1985). It is worthy to note that Schöllkopf commented, "3,4-Epoxy amino acids or their esters are so far unknown. They are potential 'suicide inhibitors' of pyridoxal phosphate depending enzymes. The problem, however, might be to hydrolyze the ester function . . . without touching the oxirane ring." The present invention, among its other novel features and advantages, solves the problem identified by Schöllkopf by allowing both the simultaneous protection of the amino and carboxyl groups (as well as any hydroxyl or amino groups on the side chains) with hydrogenolytically removable protecting groups and the simultaneous removal of the protecting groups without affecting the oxirane ring. Thus, the invention teaches the first process for producing fully deprotected α-oxiranyl amino acids.

The predicted mechanisms of enzyme inactivation by these compounds are depicted in Scheme 3 (below).

Scheme 3:
Proposed Decarboxylation/Ring Opening Mechanism:
Ring Opening Driven by Hydrogen Bonding and Relief of Ring Strain

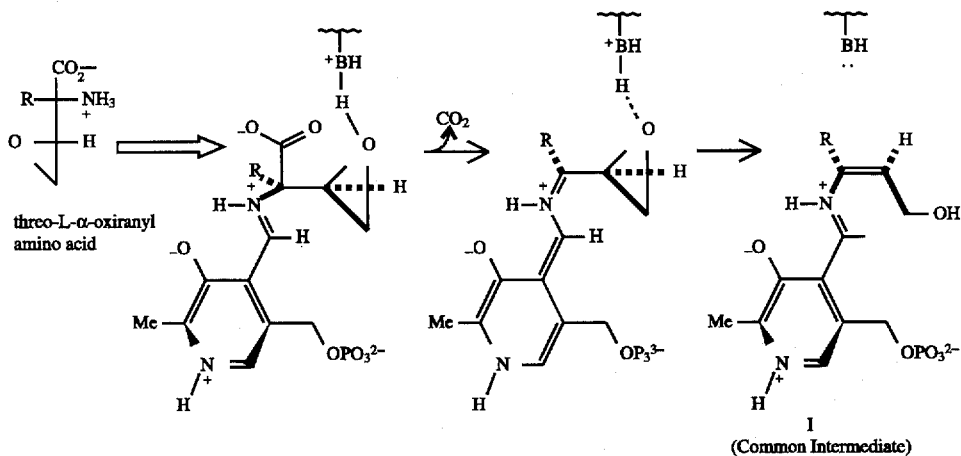

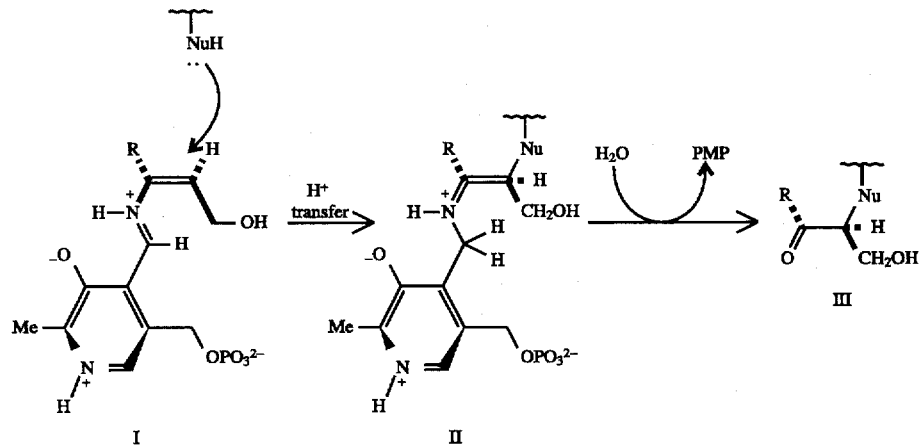

-continued
Scheme 3:
Proposed Decarboxylation/Ring Opening Mechanism:
Ring Opening Driven by Hydrogen Bonding and Relief of Ring Strain
Mechanism B: Cyclic N,O-Acetal Formation (Cofactor-Inhibitor Adduct)
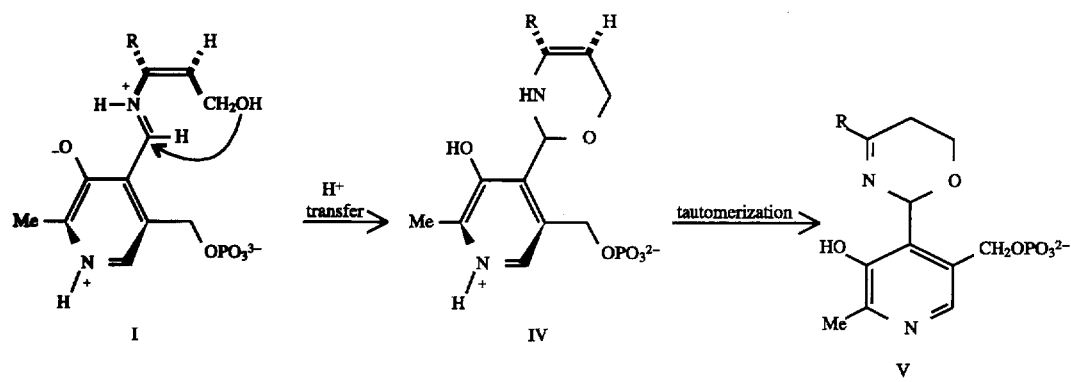
Mechanism C: α,β-Unsaturated Iminium Ion Formation/Michael Addition (Enzyme-Inhibitor Adduct)
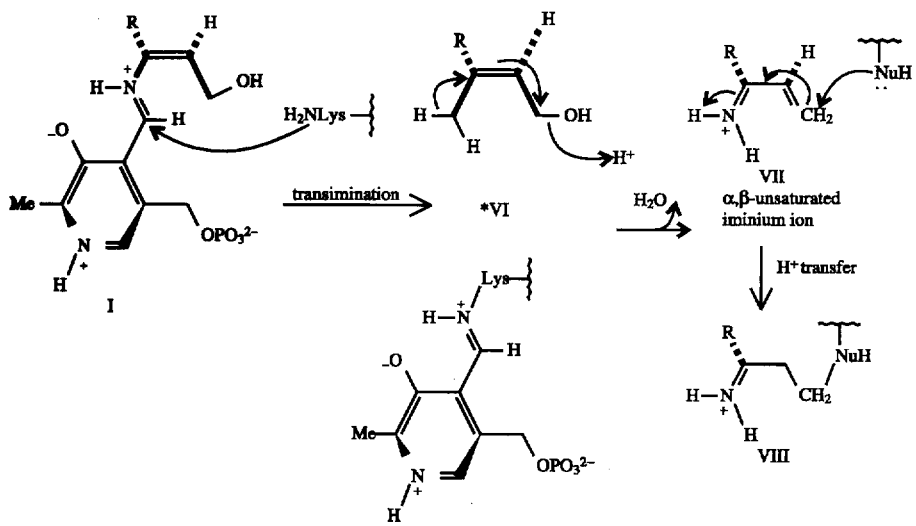

-continued
Scheme 3:
Proposed Decarboxylation/Ring Opening Mechanism:
Ring Opening Driven by Hydrogen Bonding and Relief of Ring Strain

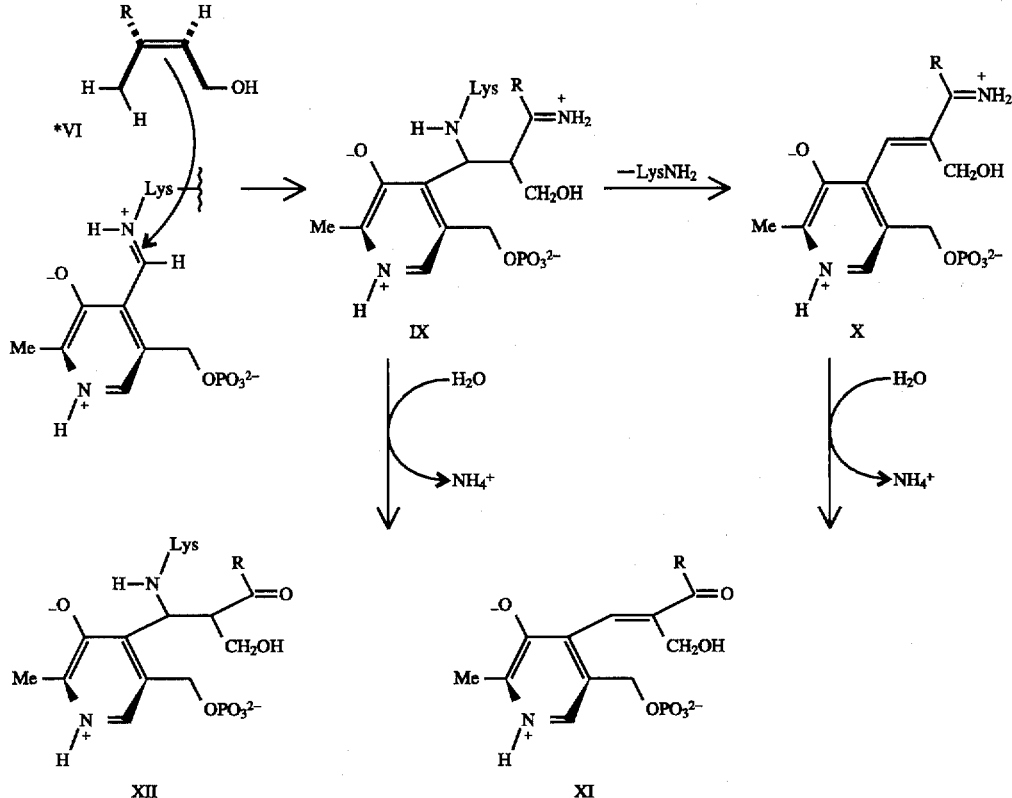

Several features are noteworthy. First, these inhibitors have a two-step trigger. Analogous to the β,γ-unsaturated amino acids, they require both decarboxylation and protonation-precisely the two normal catalytic steps to inhibit. Unlike the β,γ-unsaturated amino acids, however, partial protonation in the form of a hydrogen bond from the requisite enzymatic general acid to the epoxide oxygen is possible. While not bound by any theory, protonation of the ring heteroatom is expected to facilitate ring opening, following enzymatic decarboxylation. This ring-opening step is thought to be thermodynamically driven by relief of ring strain [18 kcal/mol (for S) to 28 kcal/mol (for O and N). Further, this sequence is expected to lead to enzyme inactivation as depicted in Scheme 3 (above).

Four inactivation pathways have been conceived, all of which emanate from the common mechanistic intermediate I. The first of these, Mechanism A, is a direct Michael addition mechanism of the type postulated for both β,γ-unsaturated amino acids and α-halogenmethyl amino acids. This mechanism is, of course, closely related to the Michael addition-elimination mechanism that appears to be operative in the case of DFMO and α-trifluoromethylalanine (Scheme 2, above).

Mechanism D corresponds to the Metzler enamine mechanism (Scheme 1above) in the context of the present inhibitor design. Although unimportant to the enablement of the present invention, this mechanism of inhibition is unlikely because the enamine (VI) that would be released by transimination, bears a hydroxyl group to the nitrogen. This enamine is expected to readily eliminate a molecule of $H_2O$ to generate an α,β unsaturated iminium ion in the active site (Mechanism C). Such a potent electrophile would likely be rapidly intercepted by an enzyme nucleophile in a Michael fashion. As this indirect Michael addition pathway is unavailable to the α-halogenmethyl amino acids, it represents a potentially important advantage of the inhibitors proposed herein.

Another plausible inhibition pathway available to the α-oxiranyl inhibitors, referred to herein as Mechanism B, postulates that the hydroxyl group δ to the imine carbon in intermediate I, cyclizes upon that carbon so as to form a six-membered N,O-acetal (Mechanism B). This pathway looks particularly advantageous for the L-threo stereoisomer, if the enzyme aligns the $C_\alpha$-$CO_2$ bond with the pyridoximine π-system above the si-face of the imine (as shown in Scheme 3). Conversely, if the enzyme aligns the $C_\alpha$-$CO_2$ bond with the pyridoximine π-system above the re-face of the imine, the D-threo diastereomer would appear most likely to cyclize. Only for Mechanism B is there a compelling argument to favor one diastereomer (threo) over the other, a priori. Of course, the ability of the epoxide oxygen to hydrogen bond with the requisite enzymatic general acid is likely to be different for the two diastereomers and manifest itself in more efficient ring-opening, and hence inactivation, for the favored diastereomer. Hence, for Mechanism B, inhibition would result from the formation of tightly bound, noncovalent complex between the cofactor-inhibitor adduct and the enzyme, analogous to the complex implicated in the inhibition of the Ser→Ala322 mutant of histidine DC by α-fluoromethylhistidine.

Schöllkopf raised concern about the possible instability of such α-oxiranyl amino acids. Id. However, Sailer et al. have recently isolated a naturally occurring substituted α-oxiranyl amino acid, flavovirin (Sailer, M.; Sasek, V.; Sejbal, J.; Budesinky, M.; Musilek, V. "Flavovirin-A New Antifungal Antibiotic Produced by the Pyrenomycete *Melanconis flavovirens*." *J. Basic Microbiol* 1989, 29:375-381). Flavovirin is apparently stable to formic acid and to pyridine and was isolated as the free zwitterion. Interestingly, the compound is an antibiotic and is highly active against yeasts.

While mechanism elucidation may prove important in studies prompted by the present disclosure, such an understanding is not important to those seeking to practice the present invention where there is disclosed a process for producing α-oxiranyl amino acids, bearing side chains of proteinogenic amino acids, in a completely deprotected form.

DETAILED DESCRIPTION a. α-Oxiranyl Amino Acids

The present invention is related to compounds useful as decarboxylase enzyme inhibitors. These compounds have the general formula

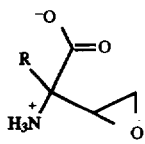

wherein R is selected from the side chains of any of the naturally occurring or synthetic proteinogenic amino acids commonly found or synthesized. R may be any straight or branched chain alkyl or aryl (including heterocyclic aryl) group and R may bear any of the following functional groups: ether, aldehyde, ketone, acetal, ketal, ester, amide, carbamate, nitrile, nitro, nitroso, phosphate, phosphonate, phosphinate, sulfone, sulfonate, sulfate or halide. R may also be the side chain of S-adenosylmethionine or its analog in which the sulfur atom is replaced by nitrogen. Examples of the naturally occurring proteinogenic amino acids are glycine, alanine, valine, leucine, isoleucine, phenlyalanine, tryptophan, serine, threonine, tyrosine, asparargine, glutamine, aspartic acid, glutamic acid, lysine, arginine, and histidine. Examples of other amino acids are m-tyrosine, DOPA, homoserine, ornithine, S-adenosylmethionine and the like.

b. Process for the Synthesis of α-Oxiranyl Amino Acids (1) The Starting Material: α-Vinyl- α-Amino Acids.

α-Oxiranyl amino acids have been synthesized according to the present invention from the corresponding α-vinyl amino acids. It will be recognized by those skilled in the art that α-vinyl amino acids are valuable in and of themselves, as several are known irreversible decarboxylase inhibitors (Table 1, above). The α-vinylation of amino acid derived carbanions is perhaps the most direct synthetic route to these vinyl compounds. There are examples of this strategy in the literature, in which either phenylsulfonyl-activated Michael acceptors or α-silylated acetaldehydes serve as vinyl cation equivalents. Sawada, S.et al., *J. Org. Chem* 51: 3384–1986); Huldrik, P. F. et al, *J. Am. Chem. Soc.* 103:625–53 (1981); Steglich, W. et al, *Synthesis* 1980, 481–83; Metcalf, B. W., et al., *J. Chem Soc. Chem. Commun.*, 914–15 (1978)

A conceptually different approach is discussed herein wherein a readily available electrophile, ethylene oxide, serves as the vinyl cation equivalent (Scheme 4, below).

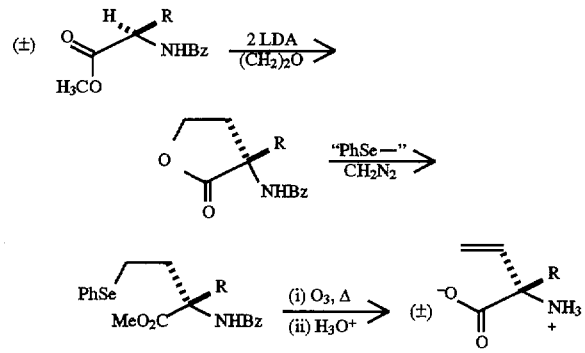

This chemistry has been applied to the synthesis of awinyl analogs of alanine, phenylalanine, valine, homoserine, omithine, lysine, arginine, histidine, aspartate and DOPA. The overall yield obtained for this sequence compares favorably to previously reported yields for the α-vinylation of protected amino acids and the scope is much broader. Furthermore, the use of ethylene oxide as vinyl cation equivalent eliminates the need to synthesize a vinyl cation equivalent. Hence, this procedure is arguably the method of choice for the formal α-vinylation of amino acids.(Scheme 4, above)

Given the chemical versatility of the vinyl functionality, these derivatives may be viewed as simple building blocks for more complex, chain extended, (α-branched amino acids. Such schemes require the presence of suitable protecting groups for the amino and carboxyl groups.

(2) THE PROTECTION STEP:Simultaneous Amino (Cbz) and Carboxyl (Bn) Protection for α-Branched Amino Acids Our initial approach to α-oxiranyl amino acids was to epoxidize suitably protected α-vinyl amino acids. Considering the potential instability of these target molecules, we chose to employ protecting groups which could be removed under mild conditions. Specifically, we envisioned the use of hydrogenolytically removable benzyloxycarbonyl (Cbz) and benzyl ester (Bn) protecting groups for the amino and carboxyl groups, respectively. However, initial attempts to introduce the benzyloxycarbonyl (Cbz) group onto the α-amino group of free α-vinyl amino acids using the usual Schotten-Baumann conditions [CbzCl, NaOH (aq)] met with little success. Under these conditions, benzyl chloroformate is apparently hydrolyzed faster than it reacts with the α-amino group of α-vinyl amino acids. Other established N-benzyloxycarbonylation reagents, including O-benzyloxycarbonyl-N-hydroxysuccinimide (Z-OSu) and [p-(benyzyloxycarbonyloxy)-phenyl]dimethylsulfonium methyl sulfate (Z-ODSP), also failed, presumably due to the sterically congested environment about the amino group. Indeed, the problems associated with amino group carbonylation for α-branched amino acids are well known and have been described by others (Turk, J.; Panse, G. T.; Marshall, G. R. *J. Org. Chem.* 40:953–955 (1975)).

In view of the report by Whitesides and coworkers that α-methyl amino acids could be N-chloroacetylated by refluxing with chloroacetyl chloride in acetonitrile (Chenault, H. K.; Dahmer, J.; Whitesides, G. M. *J. Am.*

Chem. Soc. 111:6354–6364 (1989)), and presuming that use of an organic solvent would prolong the lifetime of CbzCl in the reaction mixture and thereby facilitate the desired N-benzyloxycarbonylation, we heated α-vinyl amino acids with CbzCl in a variety of polar organic solvents (CH$_3$CN, DMF, DMPU, HMPA, DMSO). The best results were obtained with CbzCl, NEt$_3$, and catalytic DMAP, in DMSO at 50° C. Under these conditions, provided that excess CbzCl was present, both the α-amino (Cbz) and α-carboxyl (Bn) groups could be protected in a single step, in good yield (Table 2, below). Furthermore, amino (α-vinylornithine and α-vinyllysine), and hydroxylic (α-vinyl-DOPA) side chains could also be protected as the corresponding carbamates or carbonates in the same pot, given sufficient CbzCl. (Table 2, below)

those cases, an α-proton is always present. Thus Kim's procedure has not been applied to the simple esterification of (more hindered) N-protected α-branched α-amino acids. By contrast, this is the first report of the simultaneous conversion of an amine to a carbamate (N-benzyloxycarbonylation) and an acid to an ester (benzyl esterification) of an α-amino acid in a single synthetic step. All of our examples are for zwitterionic, free amino acids that are not soluble in CH$_2$Cl$_2$. Further, our procedure requires heating the amino acids in dimethylsulfoxide (DMSO) at 50° C. Many other solvents were examined and found to work much less well than DMSO or not at all. We believe the reason our procedure works better for α-vinyl α-amino acids than for usual α-amino acids (bearing an α-proton), even though the former have considerably more hindered carboxyl and

TABLE 2

Simultaneous Amino and Carboxyl Group Protection for α-Vinyl Amino Acids

| Series | α-Vinyl Amino Acid | Equiv. CbzCl | Product | | Yield |
|---|---|---|---|---|---|
| Alanine | | 3.5 | | 17 | 62% |
| Valine | | 3 | | 18 | 73% |
| Phenylalanine | | 3 | | 19 | 82% |
| Ornithine | | 5 | | 20 | 62% |
| Lysine | | 5 | | 21 | 60% |
| DOPA | | 8 | | 22 | 47% |

The benzyl esterification presumably proceeds via the mixed anhydride. This sort of esterification chemistry finds some analogy in the work of Kim [Kim, S.; Lee, J. E.; Kim, Y. C., J. Org. Chem 50:560–565 (1985)]. However, there are significant differences between the two procedures. Kim et al. report the conversion of acids to esters only and all of their examples are for neutral acids that are soluble in methylene chloride (CH$_2$Cl$_2$) at 0° C. In all cases, if an amino group is present, it is protected, including several examples of N-protected α-amino acids. However, even in amino groups than the latter, is the greater solubility of α-vinyl amino acids in DMSO over α-unbranched α-amino acids.

The protection method described herein appears to be preparatively useful only for relatively hydrophobic amino acids, such as α-branched amino acids, presumably due to their greater solubility in DMSO. But it is precisely for α-branched amino acids, in which the amino group is particularly hindered, that this chemistry is most valuable. In support of this solubility argument, a qualitative correlation between size of the alkyl chain and percent yield was observed. This is illustrated for several α-branched valine analogues in Scheme 5 (below).

Scheme 5

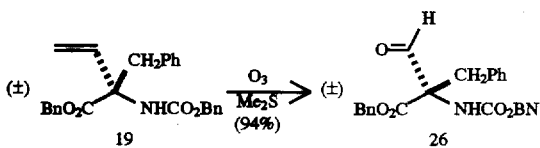

| compound | 23 | 24 | 25 | 18 |
|---|---|---|---|---|
| R | H | Me | Et | vinyl |
| yield | 21% | 41% | 54% | 73% |

In summary, this is the first report of a one pot procedure for the protection of amino acids with both carbamate (amino group) and benzyl ester protecting groups. The procedure is most efficient for relatively hydrophobic, α-branched amino acids. The nature of the carbamate and ester protecting groups could presumably be changed by simply varying the alkyl chloroformate employed. Moreover, when combined with our α-vinylation methodology, this procedure provides a direct route from α-amino acids to their N-Cbz, benzyl ester protected, α-vinyl derivatives. These, in turn, are expected to find broad application as building blocks for novel α-branched amino acids. For instance, it may be possible to directly chain-extend and functionalize these with Heck chemistry, as was recently demonstrated for N-Cbz-vinylglycine.

On the other hand, the N-Cbz-protected α-vinyl amino esters reported herein may be transformed into the corresponding α-formyl amino acids. For example, ozonolysis of 3b proceeds smoothly to yield the protected, α-formylphenylalanine, 12 (Scheme 6 below).

Scheme 6

Olefination of such protected,α-formyl amino acids would provide a complementary strategy for branch extension. Indeed, modified Wittig olefinations of related carbamate-protected (α-amino aldehydes, derived from unbranched amino acids, as well as α-branched amino acids, are well known. For such applications, hydrogenolytically cleavable protecting groups, such as those installed herein, are especially attractive, as they might be removed in the same operation in which the α-side chain is saturated.

SPECIFIC EXAMPLES OF PROTECTION STEP

General. All general experimental procedures were as described previously in the applicants' article in *Journal of Organic Chemistry*, supra. The starting α-vinyl amino acids were synthesized as reported. See Table 2, supra. These procedures are ideal for our purposes, providing epoxidation substrates in one step from completely deprotected α-vinyl amino acids

EXAMPLE NO. 1

(±)-Benzyl N-Benzyloxycarbonyl-α-vinylphenylalanine (19). To a suspension of (±)-vinylphenylalanine (560 mg, 2.9 mmol), NEt$_3$ (1.6 mL, 12 mmol) and 4-dimethylaminopyridine (71 mg, 0.59 mmol) in dry DMSO (3 mL) at 10° C. was added benzyl chloroformate (1.9 mL, 13 mmol), dropwise and with stirring. After being stirred for 1.5 h at 50° C., the reaction mixture was diluted with EtOAc (150 mL) and extracted with NaHCO$_3$ (aq, 50 mL). The organic layer was further extracted with 1N HCl (50 mL) and brine (50 mL). After drying (MgSO$_4$), the volatiles were evaporated in vacuo and the residue purified by flash SiO$_2$ chromatography (10% Et$_2$O-hexane) to give 19 (1.0 g, 82%) as a white solid: mp 68°–70° C.; $^1$H NMR (500 MHz, CDCl$_3$) δ 3.33 (d, J=13 Hz, 1 H); 3.62 (d, J=13 Hz, 1 H); 5.10–5.25 (m, 4 H); 5.27 (d, J=10 Hz, 1 H); 5.28 (d, J=17 Hz, 1 H); 5.68 (s, 1 H); 6.08 (dd, J=10, 17 Hz, 1 H); 6.90–6.91 (m, 2 H); 7.10–7.20 (m, 3 H); 7.26–7.43 (m, 10 H); $^{13}$C NMR (125 MHz, CDCl$_3$) δ 40.4, 65.1, 66.5, 67.8, 116.2, 126.9, 128.1, 128.20, 128.23, 128.4, 128.5, 128.6, 130.0, 130.3, 135.0, 135.4, 136.6, 136.8, 154.4, 171.2; IR (film) 3420–3330, 1723 cm$^{-1}$; HRMS (FAB, 3-NOBA) calcd for C$_{26}$H$_{25}$NO$_4$Na (M+Na)$^+$ 438.1681, obsd 438.1685. Anal. Calcd for C$_{26}$H$_{25}$NO$_4$: C, 75.16; H, 6.07; N, 3.37. Found: C, 74.98; H, 6.22; N, 3.37.

Compounds 17, 18 and 20–25 were synthesized analogously (all reaction times were 1.5–2 h), with the molar ratios of CbzCl and yields indicated in Table 2 (above) and Scheme 5 (above), and displayed the following spectral characteristics:

EXAMPLE NO. 2

(±)-Benzyl N-Benzyloxycarbonyl-α-vinylalaninate (17). mp 52°–54° C.; $^1$H NMR (300 MHz, CDCl$_3$) δ1.69 (s, 3 H); 5.07 (s, 2 H); 5.16 (s, 2 H); 5.22–5.25 (d, J=11 Hz, 1 H); 5.28 (d, J=17 Hz, 1 H); 5.61 (s, 1 H); 6.07 (dd, J=11, 17 Hz, 1 H); 7.28–7.40 (m, 10 H); $^{13}$C NMR (75 MHz, CDCl$_3$)δ 23.0, 60.6, 66.6, 67.5, 115.7, 127.9, 128.0, 128.1, 128.3, 128.4, 128.5, 135.4, 136.3, 137.6, 154.6, 172.3; IR (film)3352, 1716 cm$^{-1}$; HRMS (FAB, 3-NOBA) calcd for C$_{20}$H$_{22}$NO$_4$ (M+H)$^+$ 340.1549, obsd 340.1546. Anal. Calcd for C$_{20}$H$_{21}$NO$_4$: C, 70.78; H, 6.24; N, 4.12. Found: C, 70.79; H, 6.34; N, 4.18.

EXAMPLE NO. 3

(±)-Benzyl N-Benzyloxycarbonyl-α-vinylvalinate (18). mp 62°–64° C.; $^1$H NMR (300 MHz, CDCl$_3$) δ0.85 (d, J=7 Hz, 3 H); 0.86 (d, J=7 Hz, 3 H); 2.11–2.19 (m, 1H); 4.96–5.30 (m, 7 H); 6.28 (dd, J=11, 17 Hz, 1 H); 7.26–7.40 (m, 10 H); $^{13}$C NMR (125 MHz, CDCl$_3$) δ 16.9, 17.5, 35.4, 65.4, 66.9, 67.3, 115.5, 128.1, 128.2, 128.23, 128.4, 128.46, 128.5, 133.9, 135.6, 136.4, 155.0, 171.7; IR (film) 3448–3258, 1727 cm$^{-1}$; HRMS (FAB, 3-NOBA) calcd for C$_{22}$H$_{25}$NO$_4$Na (M+Na)$^+$ 390.1681, obsd 390.1685. Anal. calcd for C$_{22}$H$_{25}$NO$_4$: C, 71.91; H, 6.86; N, 3.81. Found: C, 72.14; H, 6.66; N, 3.91.

EXAMPLE NO. 4

(±)-Benzyl α,δ-Bis(N-benzyloxycarbonyl)-α-vinylornithinate (20). $^1$H NMR (300 MHz, CDCl$_3$) δ 1.15–1.28 (m, 1 H), 1.36–1.49 (m, 1 H), 1.98–2.10 (m, 1 H), 2.28–2.41 (m, 1H), 3.03–3.15 (m, 2 H), 4.59–4.69 (m, 1 H), 5.01–5.31 (m, 8 H), 5.82 (s, 1 H) 5.99 (dd, J=10, 17 Hz, 1 H), 7.27–7.50 (m, 15 H); $^{13}$C NMR (125 MHz, CDCl$_3$)δ 24.2, 32.0, 40.5, 64.0, 66.6, 66.7, 67.8, 115.9, 128.1 (2 C), 128.2, 128.3 (2 C), 128.4, 128.5 (2 C), 128.6, 128.7, 135.1, 136.3, 136.6, 154.2, 156.3, 171.7; IR (film) 3439–3277, 1717 cm$^{-1}$; HRMS (FAB, 3-NOBA) calcd for C$_{30}$H$_{33}$N$_2$O$_6$ (M+H)$^+$ 517.2338, obsd 517.2341.

EXAMPLE NO. 5

(±)-Benzyl α,ε-Bis(N-benzyloxycarbonyl)-α-vinyllysinate (21). $^1$H NMR (300 MHz, CDCl$_3$) δ 0.93–1.02 (m, 1 H), 1.19–1.45 (m, 3 H), 1.92–2.02 (m, 1 H), 2.24–2.34 (m, 1 H), 3.01–3.10 (m, 2 H), 4.69–4.73 (m, 1 H), 5.00–5.27 (m, 8 H), 5.87 (s, 1 H), 6.01 (dd, J=10, 17 Hz, 1 H), 7.26–7.39 (m, 15 H); $^1$C NMR (125 MHz, CDCl$_3$) δ 20.6, 29.3, 34.5, 40.3, 64.2, 66.6, 66.7, 67.6, 115.5, 128.0, 128.1, 128.3 (2 C), 128.4 (2 C), 128.5, 128.6 (2 C), 135.1, 136.3, 136.5, 136.7, 154.3, 156.4, 171.8; IR (film) 3413–3298, 1716 cm$^{-1}$; HRMS (FAB, 3-NOBA) calcd for C$_{31}$H$_{35}$N$_2$O$_6$ (M+H)$^+$ 531.2495, obsd 531.2478.

EXAMPLE NO. 6

(±)-Tris(N,O,O'-benzyloxycarbonyl)-α-vinyl-DOPA, benzyl ester (22). $^1$H NMR (300 MHz, CDCl$_3$) δ3.34 (d, J=13 Hz, 1 H); 3.64 (d, J=13 Hz, 1 H); 5.03–5.34 (m, 10 H); 5.71 (s, 1 H); 5.99 (dd, J=10, 17 Hz, 1 H); 6.71–6.75 (m, 1 H); 6.92–6.98 (m, 3 ): 7.26–7.40 (m, 20 H); $^{13}$C NMR (125 MHz, CDCl$_3$) δ 39.4, 65.0, 66.7, 68.0, 70.5, 70.6, 116.6, 122.5, 124.6, 126.9, 128.07, 128.1, 128.2, 128.3, 128.4, 128.45, 128.5, 128.57 (2 C), 128.61 (2 C), 128.64 (2 C), 128.7 (2 C), 134.7, 134.9, 136.4, 141.3, 141.9, 152.5, 152.6, 154.5, 170.7; IR (film) 3411 (br), 1767,1722 cm$^{-1}$; MS (FAB, 3-NOBA/K$_2$CO$_3$) 754 (base peak) (M+K)$^+$; HRMS (FAB, 3-NOBA) calcd for C$_{42}$H$_{38}$NO$_{10}$ (M+H)$^+$ 716.2496, obsd 716.2497.

EXAMPLE NO. 7

(±)-Benzyl N-benzyloxycarbonylvalinate (23) $^1$H NMR (500 MHz, CDCl$_3$): δ 0.84 (d, J=7 Hz, 3 H); 0.94 (d, J=7 Hz, 3 H); 2.16–2.19 (m, 1 H); 4.34–4.36 (m, 1 H); 5.10–5.20 (m, 4 H); 5.25–5.27 (m, 1 H); 7.30–7.38 (m, 10 H).

EXAMPLE NO. 8

(±)-Benzyl N-benzyloxycarbonyl-α-methylvalinate (24). From α-methylvaline: $^1$H NMR (500 MHz, CDCl$_3$) δ 0.86 (d, J=7 Hz, 3 H); 0.92 (d, J=7 Hz, 3 H); 1.58 (s, 3 H); 2.102.14 (m, 1 H); 5.02–5.18 (m, 4 H); 5.32 (s, 1 H); 7.27–7.38 (m, 10 H); $^{13}$C NMR (125 MHz, CDCl$_3$)δ 17.1, 17.2, 18.7, 35.2, 66.6, 67.0, 69.7, 128.1,128.2, 128.3, 128.4, 128.5, 128.54, 135.6, 136.3, 155.2, 173.5; IR (film) 3417–3319, 1719 cm$^{-1}$; HRMS (FAB, 3-NOBA) calcd for C$_{21}$H$_{26}$NO$_4$ (M+H)$^+$ 356.1862, obsd 356.1851.

EXAMPLE NO. 9

(±)-Benzyl N-Benzyloxycarbonyl-α-ethylvalinate (25). From α-ethylvaline: $^1$H NMR (500 MHz, CDCl$_3$)δ 0.71 (t, J=7, 15 Hz, 3 H); 0. 87 (d, 3 H, J=7 Hz); 0.93 (d, J=7 Hz, 3 H); 1.95–2.02 (m, 1 H); 2.43 (app quintet, J=7 Hz, 1 H); 2.50–2.60 (m, 1 H); 5.03–5.09 (m, 2 H); 5.15–5.21 (m, 2 H); 5.89 (s, 1 H); 7.28–7.35 (m, 10 H); $^{13}$C NMR (125 MHz, CDCl$_3$) δ 9.4, 18.4, 18.5, 25.8, 34.9, 66.8, 68.1, 68.9, 128.5, 128.7, 129.0, 129.1, 129.2, 129.3, 135.8, 137.4, 154.8, 173.8; IR (film) 3425–3352, 1717 cm$^{-1}$; HRMS (FA B, 3-NOBA) calcd for C$_{22}$H$_{28}$NO$_4$ (M+H)$^+$ 370,2018, obsd 370.2011.

EXAMPLE NO. 10

(±)-Benzyl(N-Benzyloxycarbonyl)-2-aminomalonate semialdehyde (26). Into a solution of 19 (25 mg, 60 µmol) in CH$_2$Cl$_2$ (15 mL) at −78° C. was bubbled O$_3$ until a light blue color persisted. After reductive workup with Me$_2$S (1 mL) at rt for 2 h, the volatiles were evaporated. The residue was partitioned between H$_2$O (20 mL) and EtOAc (2×20 mL). The organic extracts were then dried (MgSO$_4$), filtered and concentrated to afford 26 (23 mg, 94%): $^1$H NMR (300 MHz, CDCl$_3$) δ 3.49 (d, J=14 Hz, 1 H); 3.57 (d, J=14 Hz, 1 H); 5.07–5.24 (m, 4 H); 5.79 (s, 1 H); 6.79–6.82 (m, 2 H); 7.11–7.23 (m, 3 H); 7.26–7.44 (m, 10 H); 9.60 (s, 1 H); $^{13}$C NMR (125 MHz, CDCl$_3$) δ 37.9, 67.9, 69.2, 72.4, 128.0, 128.9, 129.0, 129.2, 129.3, 129.4, 129.5, 130.4, 130.6, 134.4, 135.0, 136.6, 155.7, 167.3, 193.3; IR (film) 3444–3300, 1729 cm$^{-1}$; HRMS (FAB, 3-NOBA) calcd for C$_{25}$H$_{23}$NO$_5$Na (M+Na)$^+$ 440.1474, obsd 440.1479.

(3) THE EPOXIDATION STEP: ALTERNATIVE PROCEDURES

The protected α-vinyl amino acids thereby obtained can be epoxidized with m-chloroperoxybenzoic acid (MCPBA) in CH$_2$Cl$_2$. The reaction shows little to no diastereoselectivity (1–1.5:1 ratios). More importantly, separation by flash chromatography of the diastereomeric protected, α-oxiranyl amino acids proved possible only for the valine-derived diastereomers. The alanine-derived diastereomers could be separated by HPLC.

In the case of the diastereomeric α-oxiranylphenylalanines, however, HPLC with normal and reverse phase (C-18) columns and a variety of eluents failed to give separation.(Scheme 7, below)

Scheme 7
Epoxidation Step:

(±) BnO—(vinyl)—R NHCbz  $\xrightarrow{\text{MCPBA, CH}_2\text{Cl}_2}$  (±) BnO—(epoxide)—R NHCBz 17–19 → (2 diastereomers) (1–1.5:1 ratio)

| | R | Yield | Diastereomers Separable? |
|---|---|---|---|
| 27a,b | CH$_3$ | 79% | Yes (by HPLC only) |
| 28a,b | CH(CH$_3$)$_2$ | 78% | Yes |
| 29a,b | CH$_2$Ph | 81% | No | a = erythro;
b = threo

This led us to examine alternate procedures for synthesizing α-oxiranyl amino acids via diastereomeric intermediates that might be more easily separated chromatographically. We have found that, in the case of phenylalanine, at least, the epoxides may be synthesized indirectly from the corresponding vic-diols. Most importantly, dihydroxylation of protected α-vinylphenylalanine leads to two diastereomeric vic-diols that are readily separated by flash silica gel chromatography:

(A) DIRECT EPOXIDATION:

In the direct epoxidation approach, the vinyl amino acids are epoxidized with m-chloroperoxybenzoic acid (MCPBA). The diastereomeric epoxides therby produced are sometimes easily separable (i.e. valine), and sometimes essentially inseparable (i.e. phenylalanine) (Scheme 7, above)

(B) INDIRECT EPOXIDATION

To ensure that the erythro and threo diastereomers could be readily separated, a second, indirect epoxidation procedure was also established. In this approach, the α-vinyl amino acid is initially converted to the diastereomeric erythro and threo vicinal diols through the agency of osmium tetroxide. The diastereomeric vicinal diols are generally more easily separated by silica gel chromatography than the corresponding diastereomeric epoxides. Once the erythro and threo diastereomers have been separated, they are individually transformed to the respective epoxides in two steps. Regiospecific mesylation of the less hindered primary hydroxyl group is achieved with methanesulfonyl chloride in pyridine-dichloromethane. This is followed by treatment with lithium diisopropylamide (LDA) in tetrahydrofuran, which gives the diastereomerically homogeneous epoxide. In the example given below, the otherwise essentially inseparable erythro and threo diastereomers of α-oxiranyl phenylalanine are obtained in diastereomerically homogeneous form by this procedure. (Scheme 8, below)

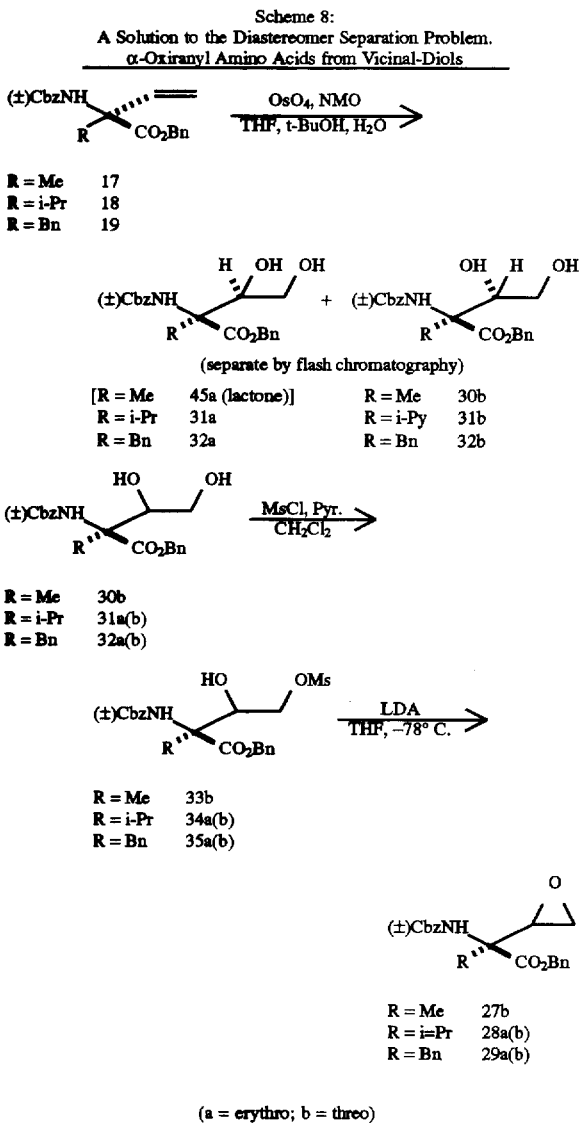

Each diastereomerically homogeneous diol in the valine and phenylalanine series has now been mesylated and cyclized to the corresponding protected, α-oxiranyl amino acid. In the alanine series, this sequence was carried out for the threo diastereomer only. The erythro diastereomer 30a lactonized to 45a at the stage of the dihydroxylation.

SPECIFIC EXAMPLES OF THE EPOXIDATION STEP

General Procedure A

Benzyl N-Benzyloxycarbonyl-α-oxiranylvalinate [(±)-28a/(±)-28b]. To a solution of (±)-18 (150 mg, 0.41 mmol)in $CH_2Cl_2$ (5 mL) at rt was added m-chloroperbenzoic acid (350 mg, 2.0 mmol). After 30 h, the reaction mixture was diluted with cold Et20 (50 mL), and washed successively with 10% $Na_2SO_3$ (aq, 30 mL) and $NaHCO_3$ (aq, sat'd, 30 mL). The organic layer was dried ($MgSO_4$), filtered and concentrated. Flash chromatography (35% EtOAc/hexane) provided the two diastereomers: (±)-28a (oil): 48 mg (31%); IR (film) 3427–3303,1724 $cm^{-1}$; $^1H$ NMR (500 MHz, $CDCl_3$) δ 0.99–1.01 (d, J=7 Hz, 3 H), 1.04–1.05 (d, J=7 Hz, 3 H), 2.34–2.39 (m, 1 H), 2.67–2.68 (m, 1 H), 2.74–2.75 (m, 1 H), 3.55 (s, 1 H), 5.00–5.10 (m, 3 H), 5.11–5.21 (m, 2 H), 7.32–7.39 (m, 10 H); $^{13}C$ NMR (125 MHz, $CDCl_3$)δ 17.5, 17.6, 34.8, 44.8, 52.5, 63.9, 66.9, 67.3, 128.2, 128.3, 128.35, 128.4, 128.5 (2 C), 128.6, 135.3, 155.2, 169.8; Anal. Calcd for $C_{22}H_{25}NO_5$: C, 68.91; H, 6.57; N, 3.65. Found: C, 69.09; H, 6.54; N, 3.71, (±)28b (white solid): 74 mg (47%); mp 74°–76° C.; IR (film) 3410–3280, 1729 $cm^{-1}$; $^1H$ NMR (500 MHz, $CDCl_3$) δ 0.97–0.99 (d, J=7 Hz, 3 H), 0.99–1.01 (d, J=7 Hz, 3 H), 2.65–2.68 (m, 2 H), 2.71–2.80 (m, 1 H), 3.57 (s, 1 H), 5.02–5.07 (app t, J=12 Hz, 2 H), 5.14–5.21 (m, 3 H), 7.29–7.40 (m, 10 H); $^{13}C$ NMR (125 MHz, $CDCl_3$)δ 17.6 (2 C), 32.5, 45.0, 52.8, 64.7, 66.9, 67.5, 128.1, 128.2, 128.4 (2 C), 128.5 (2 C), 135.2, 136.2, 155.2, 170.7; Anal. Calcd for $C_{22}H_{25}NO_8$: C, 68.91; H, 6.57; N, 3.65. Found: C, 68.81; H, 6.55; N, 3.65.

Benzyl N-Benzyloxycarbonyl-α-oxiranylalaninate [(±)-27a/(±)-27b]. From (±)-17 (16.7 mg, 0.049 mmol), following General Procedure A, was obtained a diastereomeric mixture of epoxides [137 mg, 79%; (±)-27a:(±)-27b (1:2.5)]. Separation of these diastereomers was possible by HPLC [isocratic elution with $Et_2O$/hexane/toluene (46:46:8)]. (±)-27a(white solid): mp 85°–87° C.; IR (film) 3407–3184, 1731, 1718 $cm^{-1}$; $^1H$ NMR (500 MHz, $CDCl_3$) δ 1.59 (s, 3 H), 2.74–2.75 (m, 2 H), 3.37 (s, 1 H), 5.01–5.08 (m, 2 H), 5.13–5.29(m, 3H), 7.30–7.41 (m, 10 H); $^{13}C$ NMR (75 MHz, $CDCl_3$) δ 20.7, 44.6, 54.6, 58.5, 66.9, 67.5, 128.1 (2 C), 128.2, 128.3, 128.5, 128.7, 135.3, 136.1, 155.0, 171.2; Anal. Calcd for $C_{20}H_{21}NO_5$: C, 67.59; H, 5.96; N, 3.94. Found: C, 67.41; H, 6.06; N, 3.83. (±)-27b (white solid): mp 86°–88° C.; IR (film) 3484–3296, 1734, 1717 $cm^{-1}$; $^1H$ NMR (300 MHz, $CDCl_3$) δ 1.59 (s, 3 H), 2.70–2.73 (dd, J=3,4 Hz, 1 H), 2.79–2.83 (app t, J=4 Hz, 1 H), 3.46–3.48 (dd, J=3,4 Hz, 1 H), 5.07 (s, 2 H), 5.16–5.24 (m, 2 H), 5.31 (s, 1 H), 7.34–7.40 (m, 10 H); $^{13}C$ NMR(75 MHz, $CDCl_3$) δ 19.2, 28.2, 44.3, 54.7, 66.9, 67.6, 128.0, 128.1,128.2, 128.4, 128.5, 128.6, 135.29, 135.3, 155.5, 171.9; Anal. Calcd for $C_{20}H_{21}NO_5$: C, 67.59; H, 5.96; N, 3.94. Found: C, 67.45; H, 6.04; N, 3.85.

Benzyl N-Benzyloxycarbonyl-α-oxiranylphenylalaninate [(±).29a/(±).29b]. From (±)-19 (16.7 mg, 0.049 mmol), following General Procedure A, was obtained an inseparable diastereomeric mixture of epoxides [210 mg, 81%; (±)-29a: (±)-29b (1:1.5)]. Spectral data for the individual diastereomers are tabulated below.

General Procedure B

Benzyl 2-Benzyl-2-benzyloxycarbamido-3,4-dihydroxybutanoate [(±)32a/(±)-32b]. To a solution of(±)-19 (1.00 g, 2.407 mmol) in THF (23 mL), containing 2-methyl-2-propanol (1 mL) and $H_2O$ (0.6 mL) at rt were added, $OsO_4$ (18 mg, 0.072 mmol) and 4-methylmorpholine-N-oxide (NMO)(366 mg, 3.13 mmol). After 17 h, Florisil (2 g) and NaHSO$_3$ (1.4 g) were added and the resulting suspension stirred for 30 min. Following dilution with EtOAc and filtration (Celite), the diastereomeric diols were purified by SiO$_2$ chromatography (35% EtOAc/hexane): (±)-32a (wax): (657 mg, 61%); IR (film) 3454–3279, 1732, 1689 cm$^{-1}$; $^1$H NMR (300 MHz, CDCl$_3$) δ 1.74–1.77 (m, 1 H), 3.10–3.15 (d, J=14 Hz, 1 H), 3.39–3.45 (m, 1 H), 3.59–3.65 (m, 1 H), 3.70–3.75 (d, J=14 Hz, 1 H), 4.27–4.35 (m, 1 H), 505–5.09 (d, J=12 Hz, 1 H), 5.12 (s, 2 H), 5.21–5.25 (d, J=12 Hz, 1 H), 5.35–5.39 (d, J=11 Hz, 1 H), 6.01 (s, 1 H), 6.75–6.78 (m, 2 H), 7.04–7.19 (m, 3 H), 7.31–7.41 (m, 10 H); $^{13}$C NMR (125 MHz, CDCl$_3$) δ 38.8, 64.5, 68.0, 68.2, 69.0, 73.9, 127.7, 128.9, 129.0, 129.1, 129.3, 129.33, 129.4, 129.5, 130.4, 135.1, 135.6, 136.6, 157.8, 171.6; Anal. Calcd for C$_{26}$H$_{27}$NO$_6$: C, 69.48; H, 6.05; N, 3.11. Found: C, 69.71; H, 6.10; N, 3.23. (±)-32b (white solid): (230 mg, 21%) mp 97°–99° C.; IR (film) 3482–3223, 1716 cm$^{-1}$; $^1$H NMR (300 MHz, CDCl$_3$)δ 2.19–2.28 (m, 1 H), 3.31–3.36 (d, J=14 Hz, 1 H), 3.51–3.56 (d, J=14 Hz, 1 H), 3.73–3.81 (m, 2 H), 3.82–3.90 (m, 1 H), 4.31–439 (m, I H), 4.99–5.03 (d, J=12 Hz, 1 H), 5.11–5.22 (m, 3 H), 5.65 (s, 1 H), 6.86–6.89 (m, 2 H), 7.06–7.19 (m, 3 H), 7.30–7.42 (m, 10 H); $^{13}$C NMR (125 MHz δ 37.8, 62.3, 66.9, 67.1, 68.2, 74.7, 127.2, 128.2, 128.3, 128.5, 128.6, 128.7, 128.8, 128.82, 129.8, 134.6, 134.8, 136.1, 156.0, 171.3; Anal.Calcd for C$_{26}$H$_{27}$NO6: C, 69.48; H, 6.05; N, 3.11. Found: C, 69.54; H, 6.04; N, 3.15.

Benzyl 2-Benzyloxycarbamido-3,4-dihydroxy-2-(2-propyl)butanoate [(±) 31a/(±)-31b]. From (±)-18 (508 mg, 1.38 mmol), following General Procedure B, were obtained two diastereomerically pure products [(±)-31a; 103 mg, 18%; (±)-31b; 159 mg, 29% (63% overall yield based on recovered starting material)]. (±)-31a: $^1$H NMR (500 MHz, CDCl$_3$) 5 0.74–0.76 (d, J=7 Hz, 3 H), 1.11–1.13 (d, J=7 Hz, 3 H), 1.81–1.83 (m, 1 H), 2.69–2.74 (app quintet, J=7 Hz, 1H), 3.29–3.33 (m, 1 H), 3.53–3.57 (dd, J=7 Hz, 1 H), 4.31–4.36(m, 1 H), 5.03–5.10 (dd, J=12 Hz, 2 H), 5.15–5.23 (dd, J=12 Hz, 2 H), 5.58–5.60 (d, J=11, 1 H), 6.36 (s, 1 H), 7.30–7.40 (m, 10 H). (±)-31 (500 MHz, CDCl$_3$) δ 0.85–0.87 (d, J=7 Hz, 3 H), 0.95–0.97 (d, J=7 Hz, 3 H), 2.45–2.53 (m, 2 H), 3.67–3.73 (m, 2 H), 4.04–4.06 (m, 1 H), 4.39–4.43 (m, 1 H), 5.03–5.10 (dd, J=12 Hz, 2 H), 5.17–5.26 (dd, J=12 Hz, 2 H), 5.61(s, 1 H), 7.31–7.14 (m, 10 H).

Benzyl 2-Benzyloxycarbamido-3,4-dihydroxy-2-methylbutanoate [(±)-30b/Lactone (±)-45a. From 17 (200 mg, 0.589 mmol), following General Procedure B, was obtained lactone (±)-45a (52 mg, 24%; apparently derived from diol (±)-30a in a first fraction, and diol (±)-30b (39 mg, 18%) in a second fraction (70% overall yield based on recovered starting material). (±)-30b: $^1$H NMR (500 MHz, CDCl$_3$) δ 1.57 (s, 3 H), 1.6–2.6 (br, 2 H), 3.64–3.68 (dd, J=6, 12 Hz, 1 H), 3.70–3.73 (dd, J=4, 12 Hz, 1 H), 4.00–4.02 (m, 1 H), 5.04–5.09 (dd, J=12 Hz, 2 H), 5.19 (s, 2 H), 5.75 (s, 1 H), 7.29–7.38 (m, 10 H). (±)-45a: $^1$H NMR (300 MHz, CDCl$_3$) δ 1.44 (s, 3 H), 3.92–3.98 (app t, J=9 Hz, 1 H), 4.46 (s, 1 H), 4.49–4.55 (app t, J=9 Hz, 1 H), 4.65–4.71 (appt, J=9 Hz, 1 H), 5.06–5.11 (d, J =12Hz, 1H),5.11–5.15(d, J=12 Hz, 1 H), 5.70 (s, 1 H), 7.30–7.41 (m, 5 H).

General Procedure C erythro-Benzyl-2-Benzyl-2-benzyloxycarbamido-3-hydroxy-4-mesyloxybutanoate [(±)-35a]. To a solution of (±)-32a (250 mg, 0.56 mmol)in CH$_2$Cl$_2$/pyridine (1:1) at −78° C., was slowly added methanesulfonylchloride (43 μL, 0.56 mmol). The reaction mixture was allowed to warm to rt over a period of 2–3 h. The reaction mixture was partitioned between 1N HCl (75 mL) and EtOAc (100 mL). The organic layer was further extracted with NaHCO$_3$ (aq, sat'd, 75 mL), then dried (MgSO$_4$), filtered and concentrated. Purification by SiO$_2$ chromatography (50% EtOAc/hexane) gave (±)-35a (237 mg, 81%) as a white solid: mp 84°–86° C.; IR (film) 3413–3245,1736.1691 cm$^{-1}$; $^1$H NMR (500 MHz, CDCl$_3$) δ 52.87 (s, 3 H), 3.08–3.11 (d, J=14 Hz, 1 H), 3.68–3.71 (d, J=14 Hz, 1 H), 4.00–4.04 (dd, J=7,11 Hz, 1 H), 4.21–4.24(dd, J=6, 11 Hz, 1 H), 4.54–4.59 (m, I H), 5.07–5.10 (d, J=12 Hz, 1 H), 5.12 (s, 2 H), 5.25–5.27 (d, J=12 Hz, 1 H), 5.67–5.70 (d, J=11 Hz, 1 H), 6.05 (s, 1 H), 6.73–6.75 (m, 2 H), 7.06–7.08 (m, 2 H), 7.15–7.18 (m, 1 H), 7.33–7.43 (m, 10 H); $^{13}$C NMR (125 MHz, CDCl$_3$) δ 37.2, 38.0, 67.3, 67.9, 68.9, 69.4, 73.3, 127.2, 128.4, 128.5, 128.6, 128.7, 128.8, 129.0, 129.1, 129.7, 134.1, 134.4, 135.6, 157.4, 170.2; Anal. Calcd for C$_{27}$H$_{29}$NO$_8$S: C, 61.47; H, 5.54; N, 2.65. Found: C, 61.37; H, 5.71; N, 2.73.

threo-Benzyl 2-Benzyl-2-benzyloxycarbamido-3-hydroxy-4-mesyloxybutanoate [(±)-35b]. From (±)-32b (250 mg, 0.56 mmol), following General Procedure C, was obtained (±)-35a (217 mg, 74%) as an oil: IR (film) 3393–3315, 1735, 1691 cm$^{-1}$; $^1$H NMR (360 MHz, CDCl$_3$) δ 1.47 (s, 1 H), 2.94 (s, 3 H), 3.38–3.40 (d, J=14 Hz, 1 H), 3.43–3.48 (d, J=14 Hz, 1 H), 4.32–4.38 (m, 1 H), 4.41–4.44 (m, 1 H), 4.64–4.70 (m, 1 H), 5.00–5.21 (m, 4 H), 5.53 s, 1 H), 6.83–6.85 (m, 2 H), 7.09–7.22 (m, 3 H), 7.31–7.42 (m, 10 H); Anal. Calcd for C$_{27}$H$_{29}$NO$_8$S: C, 61.47; H, 5.54; N, 2.65. Found: C, 61.27; H, 5.55; N, 2.69.

erythro-Benzyl 2-Benzyloxycarbamido-3-hydroxy-4-mesyloxy-2-(2-propyl)butanoate [(±)-34a]. From (±)-31a (100 mg, 0.25 mmol), following General Procedure C, was obtained crude mesylate (±)-34a of sufficient purity to be employed directly for the next step (General Procedure D, vide infra): $^1$H NMR (300 MHz, CDCl$_3$) 5 0.77–0.79 (d, J=7 Hz, 3 H), 1.12–1.14 (d, J=7 Hz, 3 H), 2.89 (s, 3 H), 3.93–3.98 (dd, J=7, 11 Hz, 1 H), 4.16–4.22 (dd, J=6, 11 Hz, 1 H), 4.59–4.63 (app t, J=6 Hz, 1 H), 5.07–5.12 (d, J=12 Hz, 1 H), 5.12–5.17 (d, J=12 Hz, 1 H), 5.17–5.25 (d, J=12 Hz, 1 H), 5.26–5.29 (d, J=12 Hz, 1 H), 6.42 (s, 1 H), 7.32–7.42 (m, 10 H).

threo-Benzyl 2-Benzyloxycarbamido-3-hydroxy-4-mesyloxy-2-(2-propyl)butanoate [(±)-34b]. From (±)-31 b (147 mg, 0.37 mmol), following General Procedure C, was obtained crude mesylate (±)-34b of sufficient purity to be employed directly for the next step (General Procedure D, vide infra).

threo-Benzyl 2-Benzyloxycarbamido-3-hydroxy-4-mesyloxy-2-methylbutanoate [(±)-33b]. From (±)-30b (92 mg, 0.25 mmol), following General Procedure C, was obtained crude mesylate (±)-33b of sufficient purity to be employed directly for the next step (General Procedure D, vide infra).

General Procedure D erythro-Benzyl N-Benzyloxycarbonyl-α-oxiranylphenylalaninate [(±)-29a]. To a solution of diisopropylamine (86 mL, 0.61 mmol) in THF (8 mL) at −78° C. was added n-butyllithium (380 μL, 1.6M in n-hexane), and the resulting solution stirred for 30 min at 0° C. To the LDA solution thereby generated at −78° C. was added via cannula, a solution of (±)-35a (293 mg, 0.55 mmol) in THF (8 mL). The resulting reaction mixture was allowed to slowly warm up to rt, and was then partitioned between EtOAc (50 mL) and 1N HCl (50 mL). The organic layer was dried (MgSO$_4$), filtered and concentrated. Flash chromatography (50% EtOAc/hexane) provided (±)-29a (173 mg, 72%) as a white solid: mp 90°–92° C.; IR (film) 3411–3298, 1736, 1721cm¹; ¹H NMR (300 MHz, CDCl₃)δ 2.74–2.76 (m, 1 H), 2.83–2.86 (m, 1 H), 3.27–3.32 (d, J=13 Hz, 1 H), 3.45 (s, 1 H), 3.45–3.50 (d, J=13 Hz, 1 H), 5.06–5.10 (d, J=12 Hz, 1 H), 5.12–5.16 (d, J=12 Hz, 1 H), 5.19 (s, 2 H), 5.31(s, 1 H), 6.99–7.01 (m, 2 H), 7.13–7.24 (m, 3 H), 7.29–7.43 (m, 10 H); ¹³C NMR (125 MHz, CDCl₃) δ 38.7, 44.6, 53.6 62.7, 66.8, 67.8, 127.1, 128.20, 128.23, 128.3, 128.4, 128.5 (2 C), 128.6, 130.1, 134.5, 134.9, 136.2, 154.9, 169.9; Anal. Calcd for C₂₆H₂₅NO₅: C, 72.36; H, 5.84; N, 3.24. Found: C, 72.55; H, 6.07; N, 3.21.

threo-Benzyl N-Benzyloxycarbonyl-α-oxiranylphenylalaninate [(±)-29b]. From (±)-35b (130 mg, 0.25 mmol), following General Procedure D, was obtained, after chromatography (50% EtOAc/hexane), (±)-29b (75 mg, 70%): ¹H NMR (300 MHz, CDCl₃) δ 2.43–2.48 (m, 1 H), 2.71–2.76 (m, 1 H), 3.40–3.45 (m, 1 H), 3.46–3.50 (d, =14 Hz, 1 H), 3.64–3.69 (d, J=14 Hz, 1 H), 5.04–5.08 (d, J=12 Hz, I H), 5.11–5.15 (d, J=12 Hz, 1 H), 5.21–5.25 (m, 2 H), 5.32 (s, 1 H), 6.92–6.94 (m, 2 H), 7.05–7.24 (m, 3 H), 7.29–7.42 (m, 10 H);Anal. Calcd for C₂₆H₂₅NO₅:C, 72.36;H, 5.84; N, 3.24. Found: C, 72.17; H, 5.89; N, 3.29.

erythro-Benzyl N-Benzyloxycarbonyl-α-oxiranylvalinate [(±)-28a]. From crude mesylate (±)-34a, following General Procedure D, was obtained (±)-28a (57.5 mg, 44%-2 step yield) after chromatography (50% EtOAc/hexane). This material displayed identical spectral characteristics to that obtained by direct epoxidation (vide supra).

threo-Benzyl N-Benzyloxycarbonyl-α-oxiranylvalinate [(±)-28b]. From crude mesylate (±)-34b, following General Procedure D, was obtained (±)-28b (76.5 mg, 40%-2 step yield) after chromatography (50% EtOAc/hexane). This material displayed identical spectral characteristics to that obtained by direct epoxidation (vide supra).

threo-Benzyl N-Benzyloxycarbonyl-α-oxiranylalaninate [(±)-27b]. From crude mesylate (±)-33b, following General Procedure D, was obtained (±)-27b (33.5 mg, 38%-2 step yield) after chromatography (50% EtOAc/hexane). This material displayed identical spectral characteristics to that obtained by direct epoxidation (vide supra).

(3) THE DEPROTECTION STEP

In the final step, the protecting groups (Bn or CO₂Bn) are removed hydrogenolytically to produce the fully deprotected, α-oxiranyl amino acids. There are characterized by ¹ H NMR in D₂O and HRMS.

We have found that hydrogenation of both diastereomerically homogeneous α-oxiranylvalines and of both diastereomerically homogeneous α-oxiranyl phenylalanines cleanly yields the corresponding free α-oxiranyl amino acids. (See Scheme 9, below)

Scheme 9: Deprotection Step.

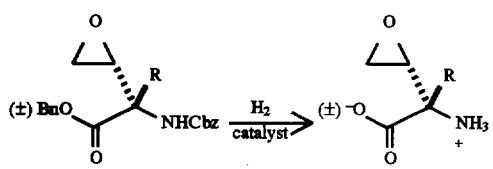

| R = Me | 27a | R = Me | 36a | (98%) |
| R = i-Pr | 28a | R = i-Pr | 37a | (98%) |
| | 28b | | 37b | (99%) |

-continued

Scheme 9: Deprotection Step.

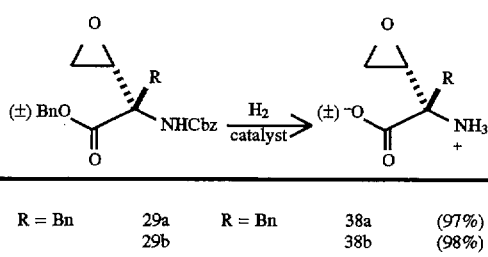

| R = Bn | 29a | R = Bn | 38a | (97%) |
| | 29b | | 38b | (98%) |

(a = erythro; b = threo)

Comparison of the ¹H and ¹³C NMR spectra of these compounds with the data reported for flavovirin supports this structure assignment. No evidence for cyclization to the γ-lactones (Baldwin-disfavored) or to the β-lactones is seen. The stability of one α-oxiranyl amino acid (α-oxiranylvaline; threo diastereomer) was also studied as a function of pH. Interestingly, this α-oxiranyl amino acid is (i) completely stable in D₂O for at least one month; (ii) completely stable at pH 3 (DCl/100 mM NaPO₄ buffer) for one week; and (iii) stable to pH 12.6 (100 mM NaPO₄ buffer) for several days, as judged by ¹H NMR.

SPECIFIC EXAMPLES OF THE DEPROTECTION STEP

General Procedure E erythro-α-Oxiranylvaline [(±)-37a]. A solution of (±)-28a (50 mg, 0.13 mmol) in CH₃OH (5 mL) containing 20% Pd(OH)₂ on carbon (7 mg) was stirred, under H₂ atmosphere, at rt for 45 min to give (±)-37a (21 mg, 98%): ¹H NMR (300 MHz, D₂O) δ 1.02–1.04 (d, J =7 Hz, 3 H), 1.10–1.13 (d, J=7 Hz, 3 H), 2.46–2.51 (app quintet, J=7 Hz, 1 H), 2.87–2.89 (app t, J=3 Hz, 1 H), 2.94–2.96 (app t, J=4 Hz, 1 H), 3.51–3.53 (dd, J=3,4 Hz, 1 H); ¹³C NMR(125 MHz, D₂O) δ 16.5, 17.3, 34.4, 44.2, 54.4, 67.1, 173.7; HRMS (FAB, 3-NOBA) calcd for C₇H₁₄NO₃ (M+H)⁺ 160.0974, obsd 160.0970.

threo-α-Oxiranylvaline [(±)-37b]. From (±)-28b (100 mg 0.261 mmol), following General Procedure E, was obtained (±)-37b (41.1 mg, 99%): ¹H NMR (500 MHz, D₂O) δ 1.04–1.06 (d, J=7 Hz, 3 H), 1.07–1.09 (d, J=7 Hz, 3 H), 2.43–2.46 (app quintet, J=7 Hz, 1 H), 2.92–2.93 (app t, J=3 Hz, 1 H), 3.11–3.13 (app t, J=4 Hz, 1 H), 3.64–3.66 (dd, J=3, 4 Hz, 1 H); ¹³C NMR (125 MHz, D₂O)δ 16.7, 17.4, 32.2, 45.8, 54.9, 67.6, 174.0; HRMS (FAB, 3-NOBA) calcd for C₇H₁₄NO₃ (M+H)⁺ 160.0974, obsd 160.0974.

erythro-α-Oxiranylphenylalanine [(±)-38a]. From (±)-29a (50 mg, 0.12 mmol), following General Procedure E, was obtained (±)-38a (24 mg, 100%): ¹H NMR (500 MHz, D₂O) δ 3.00–3.03 (app t, J=4 Hz, 1 H), 3.04–3.06 (app t, J=3 Hz, 1 H), 3.21–3.26 (d, J =14 Hz, 1 H), 3.46–3.51 (d, J=14 Hz, 1 H), 3.56–3.59dd, J=3, 4 Hz, 1 H), 7.31–7.34 (m, 2 H), 7.40–7.45 (m, 3 H); ¹³C NMR (75 MHz, D₂O) 5 40.5, 45.3, 54.6, 69.5, 128.7, 129.8, 130.8, 133.8, 174.1.

threo-α-Oxiranylphenylalanine [(±)-38b]. From (±)-29b (27 mg, 63 μmol), following General Procedure E, was obtained (±)-38b (13 mg, 100%): ¹H NMR (500 MHz, D₂O) δ 2.92–2.94 (app t, J=3 Hz, 1 H), 3.01–3.05 (d, J=14 Hz, 1 H), 3.04–3.07 (app t, J=4 Hz, 1 H), 3.32–3.37 (d, J=14 Hz, 1 H), 3.64–3.67 (dd, J=3, 4 Hz, 1 H), 7.26–7.29 (m, 2 H), 7.37–7.42 (m, 3 H); ¹³C NMR (125 MHz, D₂O) δ 38.2, 45.8, 55.0, 64.9, 128.9, 129.9, 131.0, 133.8, 171.4.

etythro-δ-Oxiranylalanine [(±)-36a]. From (±)-27a (50 mg, 0.14 mmol), following General Procedure E, was obtained (±)-38a (18 mg, 98%): $^1$NMR (300 MHz, D$_2$O) δ 1.60 (s, 3 H), 2.96–3.01 (m, 2 H), 3.42–3.45 (dd, J=3,4 Hz, 1 H); $^{13}$C NMR (75 MHz, D$_2$O)δ 20.2, 45.7, 55.0, 63.4, 174.5.

Thus, we have established (i) an efficient synthesis of α-vinyl amino acids from the parent amino acids; and (ii) two independent routes from these to the target α-oxiranyl amino acids. Taken together, this work has established a straightforward procedure for transforming a given amino acid into two diastereomerically homogeneous threo and erythro α-oxiranyl amino acids.

(4) DETERMINATION OF THE RELATIVE STEREOCHEMISTRY

The relative stereochemistry of each of the α-oxiranyl amino acids synthesized could be deduced from cyclization experiments performed on the protected vicinal diols produced in the osmylation step. Thus, treatment of diols 31a and 32a with NaH in DMF yielded the bicyclic oxazolidinones 40a and 41a, respectively (see Scheme 10, below). Two cyclizations had occurred, leading to the formation of both a δ-lactone and an oxazolidinone ring, in a 5,5-cis-fusion, with the release of two molecules of benzyl alcohol. On the other hand, treatment of the diastereomeric diols 31 b and 32b with NaH in DMF produced the monocyclic lactones 43b and 44b, with the release of one molecule of benzyl alcohol. In the alanine series, at the dihydroxylation step, the slower-eluting(threo) diol 30b was isolated, but the faster-eluting (erythro) diol was obtained in monocyclized form, as the corresponding δ-lactone 45a. Treatment of 45a with NaH in DMF produced the bicyclic oxazolidinone 39a, whereas 30b produced only moncyclic δ-lactone 42b, under the same conditions.

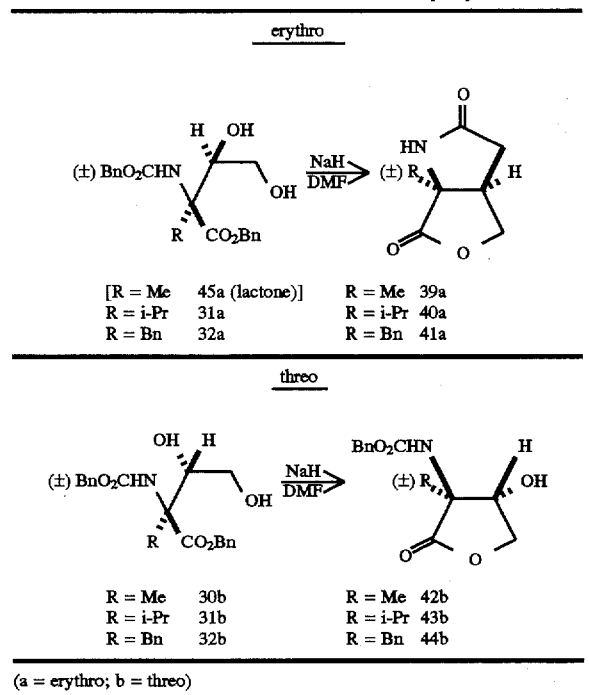

Scheme 10: Determination of Relative Stereochemistry: erythro vs threo (a = erythro; b = threo)

One can deduce from these experiments that the a series compounds have the erythro relative stereochemistry which permits the formation of the 5,5-cis fused oxazolidinonelactones 39a–41a. The b series compounds, on the other hand, must possess the threo relative stereochemistry as bicyclic oxazolidinonelactones are not formed here, because these would necessarily be highly strained, 5,5-transfused systems. Therefore, one observes only a single cyclization to the monocyclic δ-lactones 42b–44b, in these cases. On the basis of these results, the relative stereochemistry of each of the α-oxiranyl amino acids synthesized can also be deduced, as these have been chemically correlated with the corresponding vicinal diols (see Scheme 8, above).

SPECIFIC EXAMPLES OF THE CYCLIZATION STEP
(TO DETERMINE RELATIVE STEREOCHEMISTRY)

General Procedure F (±)-erythro-Oxazolidinone 41a. To a solution of (±)-32a (25 mg, 0.056 mmol) in DMF (1 mL) at 0° C. was added NaH (0.1 mg, 60% dispersion in mineral oil). The reaction mixture was slowly allowed to warm to rt, then quenched with 1N HCl (5 mL)/CH$_2$Cl$_2$ (25 mL). The organic layer was dried (MgSO$_4$), filtered and concentrated to yield (±)-41a (6.7 mg, 52%): $^1$H NMR (500 MHz, CDCl$_3$) δ 3.07–3.10 (d, J=13 Hz, 1 H), 3.40–3.43 (d, J=13 Hz, 1 H), 3.56–3.59 (dd, J=5, 11 Hz, 1 H), 4.32–4.35 (d, J=11 Hz, 1 H), 5.00–5.02 (d, J=5 Hz, 1 H), 5.65 (s, 1 H), 7.19–7.21 (m, 2 H), 7.35–7.38 (m, 3 H).

(±)-threo-Lactone 44b. From (±)-32b, following General Procedure F, was obtained (±)-44b: $^1$H NMR (360 MHz, CDCl$_3$) δ 3.03–3.05 (d, J=13 Hz, 1 H), 3.29–3.31 (d, J=13 Hz, 1 H), 3.83–3.92 (app t, J=9 Hz, 1 H), 4.41–4.50 (app t, J=9 Hz, 1 H), 4.61–4.62 (s, 1 H), 4.74–4.80 (m, 1 H), 5.05–5.07 (d, J=13 Hz, 1 H), 5.21–5.23 (d, J=13 Hz, 1 H), 5.48 (s, 1 H), 7.01–7.04 (m, 2 H), 7.21–7.38 (m, 3 H).

(±)-erythro-Oxazolidinone 40a. From (±)-31a, following General Procedure F, was obtained (±)-40a: $^1$H NMR (500 MHz, CDCl$_3$) δ 1.03–1.05 (d, J=7 Hz, 3 H), 1.05–1.07 (d, J=7 Hz, 3 H), 2.51–2.74 (app quintet, J=7 Hz, 1 H), 4.06–4.10 (app t, J=9 Hz, 1 H), 4.18–4.19 (d, J=2 Hz, 1 H), 4.48–4.52 (app t, J=9 Hz, 1 H), 4.83–4.87 (m, 1 H), 5.08–5.11 (m, 2 H), 5.69 (s, 1 H), 7.28–7.39 (m, 5 H).

(±)-threo-Lactone 43b. From (±)-31 b, following General Procedure F, was obtained (±)-43 b: $^1$H NMR (500 MHz, CDCl$_3$) δ 0.99–1.01 (d, J=7 Hz, 3 H), 1.07–1.09 (d, J=7 Hz, 3 H), 2.25–2.30 (quintet, J=7 Hz, 1 H), 4.43–4.47 (dd, J=5, 11 Hz, 1 H), 4.56–4.59 (d, J=11 Hz, 1 H), 4.95–4.97 (d, J=5 Hz, 1 H), 5.53 (s, 1 H).

(±)-erythro-Oxazolidinone 39a. From (±)-45a, following General Procedure F, was obtained (±)-39a: $^1$H NMR (300MHz, CDCl$_3$)δ 1.48 (s, 3 H), 3.02 (s, 1 H), 4.39–4.57 (m, 3 H), 5.12 (s, 2 H), 5.46 (s, 1 H), 7.33–7.39 (m, 5 H).

(±)-threo-Lactone 42b. From (±)-30b, following General Procedure F, was obtained (±)-42b: $^1$H NMR (360 MHz, CDCl$_3$) δ 1.43 (s, 3 H), 3.96–3.99 (m, 1 H), 4.12–4.16 (m, 1 H), 4.52–4.56 (m, 1 H), 4.77–4.81 (m, 1 H), 5.36 (s, 1 H).

We claim:

1. A method of synthesizing α-oxiranyl amino acids, comprising:
   (a) adding protective groups to the amino and carboxyl groups and to any hydroxyl and amino groups on side chains of an α-vinyl amino acid by heating said α-vinyl amino acids with benzyl chloroformate in dimethylsulfoxide in the presence of triethylamine and catalytic 4-dimethylaminopyridine;

(b) extracting and purifying the protected α-vinyl amino acid;

(c) converting the α-vinyl group of the protected α-vinyl amino acid obtained in step (b) to an α-oxiranyl group by epoxidation: and (d) removing the protecting groups.

2. The method of claim 1 wherein said α-vinyl amino acid is heated to approximately 50° C. with benzyl chloroformate in dimethylsulfoxide in the presence of triethylamine and catalytic 4-dimethylaminopyridine.

3. The method of claim 2 wherein said mixture is heated for approximately 1.5 hours.

4. The method of claim 1 wherein said epoxidation is a direct epoxidation.

5. The method of claim 4 wherein said direct epoxidation comprises mixing said protected amino acid with meta-chloroperoxybenzoic acid.

6. The method of claim 1 wherein said epoxidation is an indirect epoxidation.

7. The method of claim 6 wherein said indirect epoxidation comprises the steps of first converting the vinyl group to the diastereomeric erythro and threo vicinal diols through the agency of osmium tetroxide, and then separating the erythro and threo diastereomers by silica gel chromatography and then transforming these diastereomers individually to the respective epoxide by regiospecific mesylation of the less hindered primary hydroxyl group using methanesulfonyl chloride in pyridine-dichloromethane followed by treatment with lithium diisopropylamide in tetrahydrofuran to give the diastereomerically homogenous epoxide.

8. The method of claim 1 wherein said protected groups are removed by hydrogenation in the presence of a palladium catalyst.

* * * * *